United States Patent
Hoffmann et al.

(10) Patent No.: US 9,238,650 B2
(45) Date of Patent: Jan. 19, 2016

(54) SOLID FORMS OF A PYRIDO-PYRIMIDINIUM INNER SALT

(71) Applicant: E. I. DU PONT DE NEMOURS AND COMPANY, Wilmington, DE (US)

(72) Inventors: Christian Hoffmann, Newark, DE (US); Wenming Zhang, Newark, DE (US); Yuzhong Chen, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 14/410,269

(22) PCT Filed: Jun. 14, 2013

(86) PCT No.: PCT/US2013/045815
§ 371 (c)(1),
(2) Date: Dec. 22, 2014

(87) PCT Pub. No.: WO2013/192035
PCT Pub. Date: Dec. 27, 2013

(65) Prior Publication Data
US 2015/0252040 A1    Sep. 10, 2015

Related U.S. Application Data

(60) Provisional application No. 61/662,532, filed on Jun. 21, 2012.

(51) Int. Cl.
*A01N 43/90*   (2006.01)
*A61K 31/519*  (2006.01)
*C07D 239/70*  (2006.01)
*C07D 471/04*  (2006.01)
*A01N 43/78*   (2006.01)

(52) U.S. Cl.
CPC ............. *C07D 471/04* (2013.01); *A01N 43/78* (2013.01); *A01N 43/90* (2013.01); *C07B 2200/13* (2013.01)

(58) Field of Classification Search
None
See application file for complete search history.

(56) References Cited

U.S. PATENT DOCUMENTS

2012/0277100 A1   11/2012   Zhang et al.
2014/0343284 A1   11/2014   Zhang

FOREIGN PATENT DOCUMENTS

WO   2011/017342 A2   2/2011
WO   2013/090547 A2   6/2013

*Primary Examiner* — Jeffrey H Murray
(74) *Attorney, Agent, or Firm* — Roman Kucharczyk

(57) ABSTRACT

Disclosed are solid forms of 1-[(2-chloro-5-thiazolyl)methyl]-3-(3,5-dichlorophenyl)-2-hydroxy-9-methyl-4-oxo-4H-pyrido[1,2-a]pyrimidinium inner salt (Compound 1). Methods for the preparation of solid forms of Compound 1 and for the conversion of one solid form of Compound 1 into another are disclosed.

Disclosed are compositions for controlling an invertebrate pest comprising a biologically effective amount of a solid form of Compound 1 and at least one additional component selected from the group consisting of surfactants, solid diluents and liquid carriers. Compositions comprising a mixture of a solid form of Compound 1 and at least one other nematocide, insecticide and/or fungicide are also disclosed.

Also disclosed are methods for controlling invertebrate pests comprising applying to a plant or seed, or to the environment of the plant or seed, a biologically effective amount of a solid form of Compound 1.

18 Claims, 2 Drawing Sheets

SOLID FORMS OF A PYRIDO-PYRIMIDINIUM INNER SALT

FIELD OF THE INVENTION

This invention relates to solid forms of 1-[(2-chloro-5-thiazolyl)methyl]-3-(3,5-dichlorophenyl)-2-hydroxy-9-methyl-4-oxo-4H-pyrido[1,2-a]pyrimidinium inner salt, their preparation, compositions, and methods of use for controlling invertebrate pests such as arthropods in both agronomic and nonagronomic environments, and for treatment of parasite infections in animals or infestations in the general environment.

BACKGROUND OF THE INVENTION

The solid state of chemical compounds can be amorphous (i.e. no long-range order in the positions of atoms) or crystalline (i.e. atoms arranged in an orderly repeating pattern). The term "polymorph" refers to a particular crystal form (i.e. structure of crystal lattice) of a chemical compound that can exist in more than one crystal form in the solid state. Polymorphs can differ in such chemical and physical (i.e. physicochemical) properties as crystal shape, density, hardness, color, chemical stability, melting point, hygroscopicity, suspensibility, solubility and dissolution rate, and such biological properties as biological availability, biological efficacy and toxicity.

Predicting physicochemical properties such as melting point or solubility for a crystal form in which the solid state of a chemical compound can exist remains impossible. Furthermore, even predicting whether the solid state of a compound may be present in more than one crystal form is not possible.

PCT Patent Publication WO 2011/017342 discloses 1-[(2-chloro-5-thiazolyl)methyl]-3-(3,5-dichlorophenyl)-2-hydroxy-9-methyl-4-oxo-4H-pyrido[1,2-a]pyrimidinium inner salt and methods for its preparation, as well as the utility of this compound for controlling invertebrate pests. New solid forms of this compound, their compositions and methods of their preparation and use have now been discovered.

SUMMARY OF THE INVENTION

This invention relates to solid forms of 1-[(2-chloro-5-thiazolyl)methyl]-3-(3,5-dichlorophenyl)-2-hydroxy-9-methyl-4-oxo-4H-pyrido[1,2-a]pyrimidinium inner salt (Compound 1). More particularly, this invention is directed to a polymorph of Compound 1 designated Form A characterized by room-temperature powder Cu(Kα1)-X-ray diffraction pattern having at least the 2θ reflection positions 8.036, 9.592, 13.719, 14.453, 17.07, 23.092, 24.027, 24.481, 29.743 and 31.831 degrees.

This invention also relates to methods for the direct preparation of polymorph Form A of Compound 1 (i.e. not starting with other solid forms of Compound 1). More particularly, this invention is directed to a method for preparing polymorph Form A of Compound 1 comprising: forming a reaction mixture by contacting 2-(3,5-dichlorophenyl)propanedioyl dichloride and N-[(2-chloro-5-thiazolyl)methyl]-3-methyl-2-pyridinamine in the presence of a first solvent to form an intermediate solid form of Compound 1 and then optionally mixing the intermediate solid form of Compound 1 with a second solvent to convert the intermediate solid form to the polymorph Form A. Alternatively this invention is directed to a method for preparing polymorph Form A of Compound 1 comprising: forming a reaction mixture by contacting 2-(3,5-dichlorophenyl)propanedioyl dichloride and N-[(2-chloro-5-thiazolyl)methyl]-3-methyl-2-pyridinamine in the presence of a solvent optionally heated to a temperature between 30° C. and the boiling point of the solvent to form polymorph Form A of Compound 1.

This invention also relates to methods for the conversion of one solid form of Compound 1 into polymorph Form A. More particularly, this invention is directed to a method for preparing a polymorph of Compound 1 designated Form A, the method comprising: forming a slurry with a solvent of one or more solid forms of Compound 1 selected from the group of Form B, amorphous forms and mixtures thereof with Form A and maintaining the slurry while the solid forms of Compound 1 convert to polymorph Form A.

This invention also relates to a composition for controlling invertebrate pests comprising (a) polymorph Form A of Compound 1; and (b) at least one additional component selected from the group consisting of surfactants, solid diluents and liquid carriers.

This invention also relates to a composition for controlling invertebrate pests comprising (a) polymorph Form A of Compound 1; and (b) at least one other nematocide, insecticide and/or fungicide.

This invention further relates to a method of use for controlling invertebrate pests comprising applying to a plant or seed, or to the environment of the plant or seed, a biologically effective amount of Compound 1 comprising the polymorph Form A.

DETAILED DESCRIPTION OF THE INVENTION

Figure 1A:
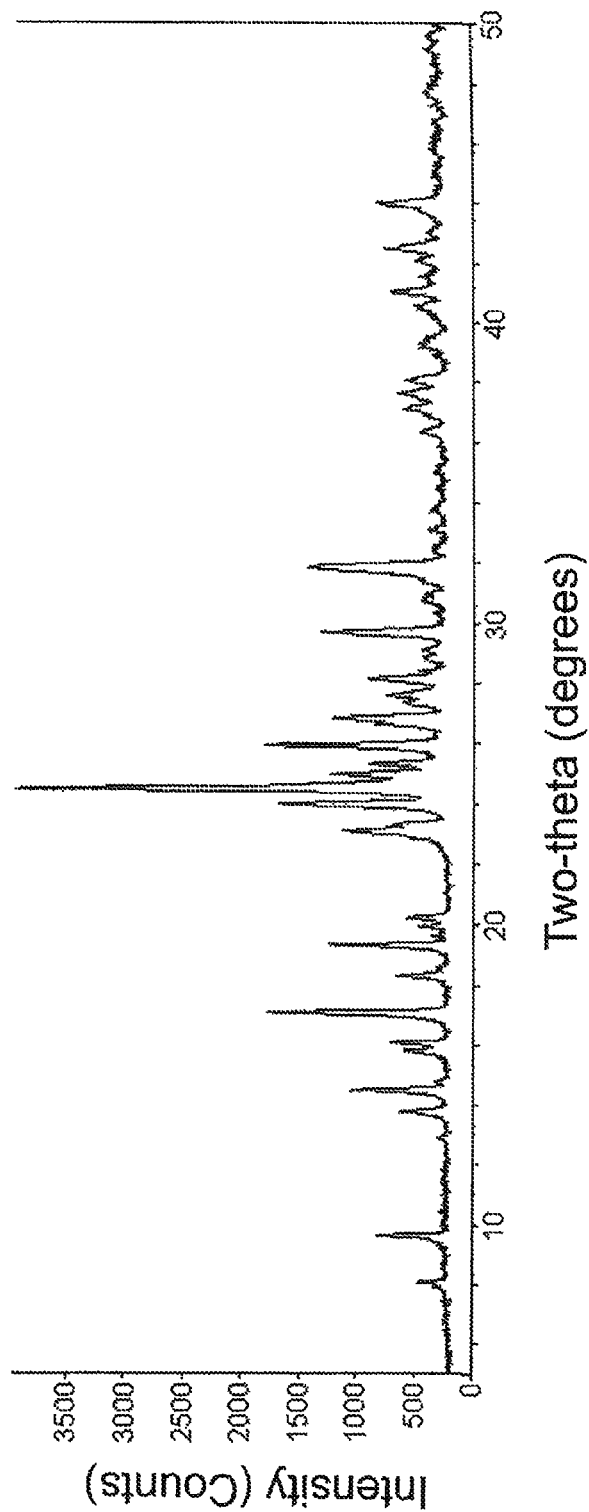
FIG. 1A shows room temperature Cu-Kα1-powder X-ray diffraction patterns of polymorph Form A of Compound 1 showing absolute X-ray intensity in counts graphed against 2θ reflection positions in degrees.

As used herein, the terms "comprises", "comprising", "includes", "including", "has", "having", "contains", "containing", "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components or elements, in addition to those literally disclosed, provided that these additional materials, steps, features, components or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising", it should be readily understood that (unless otherwise stated) the description should be interpreted to also describe such an invention using the terms "consisting essentially of" or "consisting of".

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in this disclosure, the term "invertebrate pest" includes arthropods, gastropods and nematodes of economic importance as pests. The term "arthropod" includes insects, mites, spiders, scorpions, centipedes, millipedes, pill bugs and symphylans. The term "gastropod" includes snails, slugs and other Stylommatophora. The term "nematode" refers to a living organism of the Phylum Nematoda. The term "helminths" includes roundworms, heartworms, phytophagous nematodes (Nematoda), flukes (Tematoda), Acanthocephala and tapeworms (Cestoda).

In the context of this disclosure "invertebrate pest control" means inhibition of invertebrate pest development (including mortality, feeding reduction, and/or mating disruption), and related expressions are defined analogously.

The term "agronomic" refers to the production of field crops such as for food and fiber and includes the growth of soybeans and other legumes, cereal (e.g., wheat, oats, barley, rye, rice, maize/corn), leafy vegetables (e.g., lettuce, cabbage, and other cole crops), fruiting vegetables (e.g., tomatoes, pepper, eggplant, crucifers and cucurbits), potatoes, sweet potatoes, grapes, cotton, tree fruits (e.g., pome, stone and citrus), small fruit (berries, cherries) and other specialty crops (e.g., canola, sunflower, olives).

The term "nonagronomic" refers to other than field crops, such as horticultural crops (e.g., greenhouse, nursery or ornamental plants not grown in a field), residential, agricultural, commercial and industrial structures, turf (e.g., sod farm, pasture, golf course, lawn, sports field, etc.), wood products, stored product, agro-forestry and vegetation management, public health (i.e. human) and animal health (e.g., domesticated animals such as pets, livestock and poultry, undomesticated animals such as wildlife) applications.

Nonagronomic applications include protecting an animal from an invertebrate parasitic pest by administering a parasiticidally effective (i.e. biologically effective) amount of a compound of the invention, typically in the form of a composition formulated for veterinary use, to the animal to be protected. As referred to in the present disclosure and claims, the terms "parasiticidal" and "parasiticidally" refers to observable effects on a parasitic nematode to provide protection of a plant or animal from the nematode. Parasiticidal effects typically relate to diminishing the occurrence or activity of the target parasitic nematode. Such effects on the nematode include necrosis, death, retarded growth, diminished mobility or lessened ability to remain on or in the host plant or animal, reduced feeding and inhibition of reproduction. These effects on parasitic nematodes provide control (including prevention, reduction or elimination) of parasitic infestation of the plant or animal. Therefore "control" of a parasitic nematode means achieving a parasiticidal effect on the nematode. The expressions "parasiticidally effective amount" and "biologically effective amount" in the context of applying a chemical compound to control a parasitic nematode refer an amount of the compound that is sufficient to control the parasitic nematode.

As used to in the present disclosure and claims, the term "nematode" refers to a living organism of the Phylum Nematoda. As generally defined, a "parasite" lives or grows inside or feeds on another living organism (such as a plant or animal) described as the "host". As referred to in the present disclosure and claims a "parasitic nematode" is particularly a nematode that injures or damages tissue or causes other forms of disease in plants or animals.

The word "nematocide" is sometimes given the alternative spelling "nematicide" in the art. A nematocide is a compound used to control (including prevention, reduction or elimination) parasitic nematodes.

An "infestation" refers to the presence of nematodes in numbers that pose a risk to plants or animals. The presence can be in the environment, e.g., on an agricultural crop, on a domesticated animal or on other native plants or wildlife in the area.

As referred to in the present disclosure and claims, "plant" includes members of Kingdom Plantae, particularly seed plants (Spermatopsida), at all life stages, including young plants (e.g., germinating seeds developing into seedlings) and mature, reproductive stages (e.g., plants producing flowers and seeds). Portions of plants include geotropic members typically growing beneath the surface of the growing medium such as roots, tubers, bulbs and corms, and also members growing above the growing medium, such as foliage (including stems and leaves), flowers, fruits and seeds. Growing mediums include soil, liquid nutrent mediums, gel nutrent mediums or soil mixes with peat, bark, saw dust, sand, pumice, perlite, vermiculite and other similar products. As referred to herein, the term "seedling", used either alone or in a combination of words means a young plant developing from the embryo of a seed.

The term "water-miscible" in the context of "water-miscible solvent" means a liquid solvent (including mixtures of solvent compounds) that is completely soluble in water (and water soluble in the solvent) in all proportions at the temperature of the (e.g., reaction) medium comprising the water-miscible solvent. Methanol, ethanol, acetone and acetonitrile are examples of water-miscible solvents.

Conversely, the term "water-immiscible" in the context of a substance that is a "water-immiscible organic compound", "water-immiscible liquid component" or "water-immiscible liquid carrier" denotes that the substance is not soluble in water (and water soluble in the substance) in all proportions at relevant temperatures (for formulated compositions around room temperature, e.g. about 20° C.). Typically water-immiscible substances used as liquid carriers or other liquid components in formulated compositions have little water solubility and water has little solubility in the water-immiscible substances. Often water-immiscible substances used in formulation are soluble in water in an extent of less than about 1%, or less than about 0.1%, or even less than about 0.01% by weight at about 20° C.

The expression "continuous liquid phase" in the context of liquid formulated compositions refers to the liquid phase formed by the liquid carrier. The continuous liquid phase provides the bulk liquid medium in which other formulating components are dissolved, dispersed (as solid particulates) or emulsified (as liquid droplets). When the liquid carrier is aqueous (water optionally containing dissolved water-soluble compounds), a liquid emulsified in the aqueous liquid carrier is formed by a water-immiscible liquid component.

The term "room temperature" as used in this disclosure refers to a temperature between about 18° C. and about 28° C.

The term "polymorph" refers to a particular crystal form (i.e. structure of crystal lattice) of a chemical compound that can exist in more than one crystal form in the solid state.

The compound name, potassium 2-(3,5-dichlorophenyl) propanedioate (2:1), indicates that there are two potassium cations for every one propanedioate dianion.

Embodiments of the present invention include:

Embodiment 1. The polymorph of 1-[(2-chloro-5-thiazolyl)methyl]-3-(3,5-dichlorophenyl)-2-hydroxy-9-methyl-4-oxo-4H-pyrido[1,2-a]pyrimidinium inner salt (Compound 1) designated Form A in the Summary of the Invention and characterized by room-temperature powder Cu(Kα1)-X-ray diffraction pattern having at least the 2θ reflection positions

| 2θ | 2θ |
|---|---|
| 8.036 | 23.092 |
| 9.592 | 24.027 |
| 13.719 | 24.481 |
| 14.453 | 29.743 |
| 17.07 | 31.831 |

Embodiment 2. The polymorph of 1-[(2-chloro-5-thiazolyl)methyl]-3-(3,5-dichlorophenyl)-2-hydroxy-9-methyl-4-oxo-4H-pyrido[1,2-a]pyrimidinium inner salt (Compound 1) designated Form B in the Summary of the Invention and characterized by room-temperature powder Cu(Kα1)-X-ray diffraction pattern having at least the 2θ reflection positions

| 2θ | 2θ |
|---|---|
| 6.654 | 21.225 |
| 9.41 | 22.012 |
| 10.983 | 25.638 |
| 11.986 | 28.545 |
| 15.513 | 40.244 |

Embodiment 3. The method described in the Summary of the Invention for preparing the polymorph Form A of Embodiment 1 comprising forming a slurry with a solvent of one or more solid forms of Compound 1 selected from the group of Form B, amorphous forms and mixtures of any of the foregoing with Form A and maintaining the slurry while the solid forms of Compound 1 convert to polymorph Form A.

Embodiment 4. The method of Embodiment 3 wherein the solid form of Compound 1 comprises polymorph Form B.

Embodiment 5. The method of Embodiment 3 wherein the solid forms of Compound 1 comprises a mixture of polymorphs Form A and Form B.

Embodiment 6. The method of any one of Embodiments 3 through 5 wherein seed crystals of polymorph Form A of claim 1 are added to the slurry.

Embodiment 7. The method of any one of Embodiments 3 through 6 wherein the slurry is agitated.

Embodiment 8. The method of any one of Embodiments 3 through 6 wherein the slurry is agitated and heated to a temperature between 30° C. and the boiling point of the solvent.

Embodiment 9. The method of any one of Embodiments 3 through 6 wherein the slurry is heated to a temperature between 55° C. and 110° C. and agitated.

Embodiment 10. The method of any one of Embodiments 3 through 6 wherein the slurry is heated to a temperature between 90° C. and 110° C. and agitated.

Embodiment 11. The method of any one of Embodiments 3 through 10 wherein the solvent comprises one or more of water, a $C_4$-$C_8$ ester, a $C_2$-$C_4$ alkanol, a $C_3$-$C_8$ ketone, a $C_4$-$C_8$ ether, a $C_2$-$C_7$ nitrile or a $C_7$-$C_9$ aromatic hydrocarbon.

Embodiment 12. The method of Embodiment 11 wherein the solvent comprises one or more of water, ethyl acetate, acetone, acetonitrile or toluene.

Embodiment 13. The method of Embodiment 12 wherein the solvent comprises one or more of water or toluene.

Embodiment 14. The method described in the Summary of the Invention for preparing the polymorph Form A of Compound 1 comprising, (A) contacting 2-(3,5-dichlorophenyl)propanedioyl dichloride and N-[(2-chloro-5-thiazolyl)methyl]-3-methyl-2-pyridinamine in the presence of a first solvent to form a reaction mixture containing an intermediate solid form of Compound 1, (B) optionally separating the intermediate solid form of Compound 1, and (C) contacting the intermediate solid form of Compound 1 with a second solvent optionally heated to a temperature between 30° C. and the boiling point of the second solvent to convert the intermediate solid form to the polymorph Form A of Compound 1.

Embodiment 14a. The method of Embodiment 14 wherein the intermediate solid form of Compound 1 is separated in step (B).

Embodiment 14b. The method of Embodiment 14 wherein the intermediate solid form of Compound 1 is not separated in step (B).

Embodiment 15. The method of Embodiment 14 wherein the intermediate solid form of Compound 1 comprises polymorph Form B.

Embodiment 16. The method of Embodiment 14 wherein the intermediate solid form of Compound 1 comprises a mixture of polymorphs Form A and Form B.

Embodiment 17. The method of Embodiment 14 wherein the first solvent comprises one or more of a $C_4$-$C_8$ ester or a $C_7$-$C_9$ aromatic hydrocarbon.

Embodiment 18. The method of Embodiment 17 wherein the first solvent comprises one or more of ethyl acetate or toluene.

Embodiment 19. The method of any one of Embodiments 14 through 18 wherein the second solvent comprises one or more of water, a $C_4$-$C_8$ ester, a $C_2$-$C_4$ alkanol, a $C_3$-$C_8$ ketone, a $C_4$-$C_8$ ether or a $C_7$-$C_9$ aromatic hydrocarbon.

Embodiment 20. The method of Embodiment 19 wherein the second solvent comprises one or more of water, ethyl acetate, acetone or toluene.

Embodiment 21. The method of Embodiment 20 wherein the second solvent comprises one or more of water or toluene.

Embodiment 22. The method of any one of Embodiments 14 through 21 wherein the second solvent is heated to a temperature between 55° C. and 110° C.

Embodiment 23. The method of any one of Embodiments 14 through 21 wherein the second solvent is heated to a temperature between 90° C. and 110° C.

Embodiment 24. The method of any one of Embodiments 14 through 23 wherein the first solvent and the second solvent are the same.

Embodiment 24a. The method of any one of Embodiments 14 through 24 wherein the first and second solvent comprises toluene and the second solvent is heated to a temperature between 90° C. and 110° C.

Embodiment 25. The method of any one of Embodiments 14 through 24a wherein in step (C) the intermediate solid form of Compound 1 is contacted with seed crystals of polymorph Form A of claim 1.

Embodiment 26. The method described in the Summary of the Invention for preparing the polymorph Form A of Compound 1 comprising contacting 2-(3,5-dichlorophenyl)propanedioyl dichloride and N-[(2-chloro-5-thiazolyl)methyl]-3-methyl-2-pyridinamine in the presence of a solvent optionally heated to a temperature between 30° C. and the boiling point of the solvent to form a reaction mixture containing polymorph Form A of Compound 1.

Embodiment 27. The method of Embodiment 26 wherein the solvent comprises one or more of a $C_4$-$C_8$ ester, a $C_3$-$C_8$ ketone, a $C_4$-$C_8$ ether or a $C_1$-$C_2$ chlorinated hydrocarbon.

Embodiment 28. The method of Embodiment 27 wherein the solvent comprises one or more of ethyl acetate, acetone or dichloromethane.

Embodiment 29. The method of Embodiment 28 wherein the solvent comprises dichloromethane.

Embodiment 30. The method of Embodiment 26 wherein the solvent comprises ethyl acetate and the temperature is between 55° C. and 80° C.

Embodiments of this invention, including Embodiments 1-30 above as well as any other embodiments described herein, can be combined in any manner.

Compound 1 is 1-[(2-chloro-5-thiazolyl)methyl]-3-(3,5-dichlorophenyl)-2-hydroxy-9-methyl-4-oxo-4H-pyrido[1,2-a]pyrimidinium inner salt and has the following molecular structure:

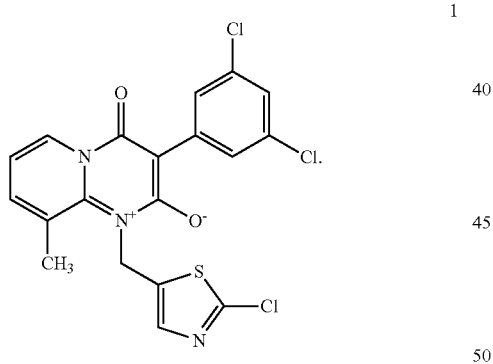

1

Compound 1 is a mesoionic inner salt. "Inner salt", also known in the art as "zwitterion", is an electrically neutral molecule but carries formal positive and negative charges on different atoms in each valence bond structure according to valence bond theory. Furthermore the molecular structure of Compound 1 can be represented by the six valence bond structures shown below, each placing the formal positive and negative charges on different atoms. Because of this resonance, Compound 1 is also described as "mesoionic". For sake of simplicity, the molecular structure of Compound 1 is depicted as a single valence bond structure herein, this particular valence bond structure is to be understood as representative of all six valence bond structures relevant to bonding in Compound 1. Therefore, reference to Compound 1 herein relates to all six applicable valence bond structures and other (e.g., molecular orbital theory) structures unless otherwise specified.

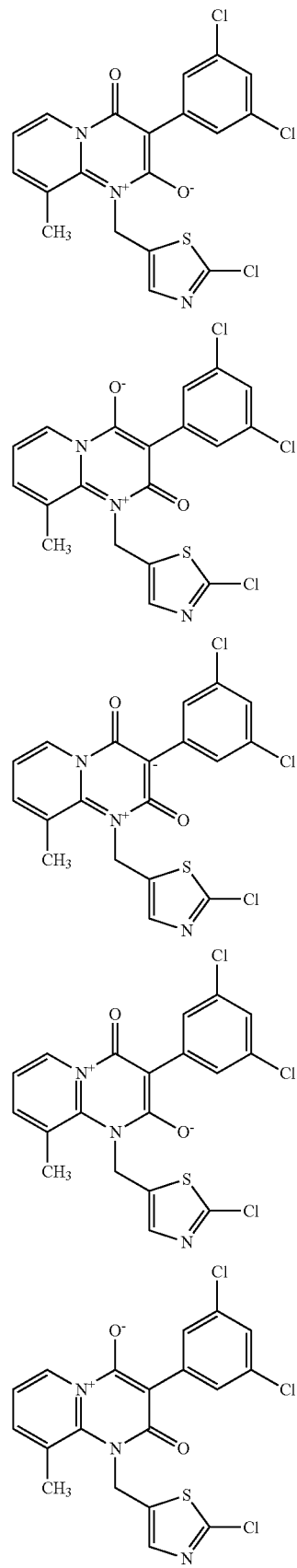

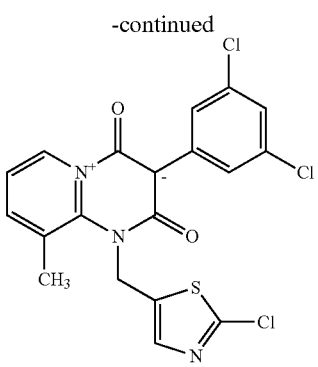

The solid state of Compound 1 has now been discovered to be preparable in more than one solid form. These solid forms include an amorphous solid form, in which there is no long-range order in the positions of molecules (e.g., foams and glasses). These solid forms also include crystalline forms, in which constituent molecules are arranged in an orderly repeating pattern extending in all three spatial dimensions. The term "polymorph" refers to a particular crystalline form of a chemical compound that can exist in more than one crystal structure (e.g. lattice type) in the solid state. The term "packing polymorphs" refers to particular crystalline forms of a compound having different crystal packing. Crystalline forms of Compound 1 in this invention relate to embodiments which include a single polymorph (i.e. single crystalline form) and to embodiments which include a mixture of polymorphs (i.e. different crystalline forms). Polymorphs can differ in such chemical, physical and biological properties as crystal shape, density, hardness, color, chemical stability, melting point, hygroscopicity, suspensibility, solubility, dissolution rate and biological availability. One skilled in the art will appreciate that a polymorph of Compound 1 can exhibit beneficial effects (e.g., suitability for preparation of useful formulations, stability, improved biological performance) relative to another polymorph or a mixture of polymorphs of Compound 1. Differences with respect to chemical stability, filterability, solubility, hygroscopicity, melting point, solid density and flowability can have a significant effect on the development of production methods and formulations, and efficacy of invertebrate pest control. Preparation and isolation of particular polymorphs of Compound 1 have now been achieved.

One crystalline polymorph form of Compound 1 is designated as polymorph Form A. This solid form is unsolvated. Polymorph Form A can be characterized by X-ray powder diffraction, single crystal X-ray structure analysis and Differential Scanning calorimetry (DSC).

The powder X-ray diffraction pattern of polymorph Form A of Compound 1 is shown in FIG. 1A. The corresponding 2θ values are tabulated in Table 4 of Characterization Example 1. Polymorph Form A of Compound 1 can be identified by a room-temperature powder Cu(Kα1)-X-ray diffraction pattern having at least the 2θ reflection positions (in degrees)

| 2θ | 2θ |
|---|---|
| 8.036 | 23.092 |
| 9.592 | 24.027 |
| 13.719 | 24.481 |
| 14.453 | 29.743 |
| 17.07 | 31.831 |

Single crystal X-ray diffraction can also be used to characterize polymorph Form A. A description of single crystal X-ray diffraction of polymorph Form A is provided in Characterization Example 3. Crystals of polymorph Form A have a monoclinic unit cell and may exhibit a variety of morphologies with needle or octahedral morphologies being most typical.

Polymorph Form A of Compound 1 can also be characterized by Differential Scanning calorimetry (DSC). DSC indicates the melting point of polymorph Form A is about 204° C. The details of a DSC experiment are provided in Characterization Example 8. Polymorph Form A is physically and chemically stable in its pure solid form (shown in Characterization Example 5).

Pure Polymorph Form A can be prepared directly during the preparation of Compound 1 in ethyl acetate (as described in Preparation Example 1) or in dichloromethane (as described in Preparation Example 3). Polymorph Form A can be prepared indirectly during the preparation of Compound 1 in toluene (as described in Preparation Example 8) by first forming Form B and then converting Form B in situ to Form A. Polymorph Form A can be prepared from isolated polymorph Form B or mixtures of Forms A and B by forming a slurry of the polymorphs in a solvent with optional heating and then cooling back to room temperature or lower as described in Preparation Examples 4, 5, 6 and 7.

Another crystalline polymorph form of Compound 1 is designated as Polymorph Form B. This solid form is unsolvated. Polymorph Form B can be characterized by X-ray powder diffraction, single crystal X-ray structure analysis and Differential Scanning Calorimetry.

Figure 1B:
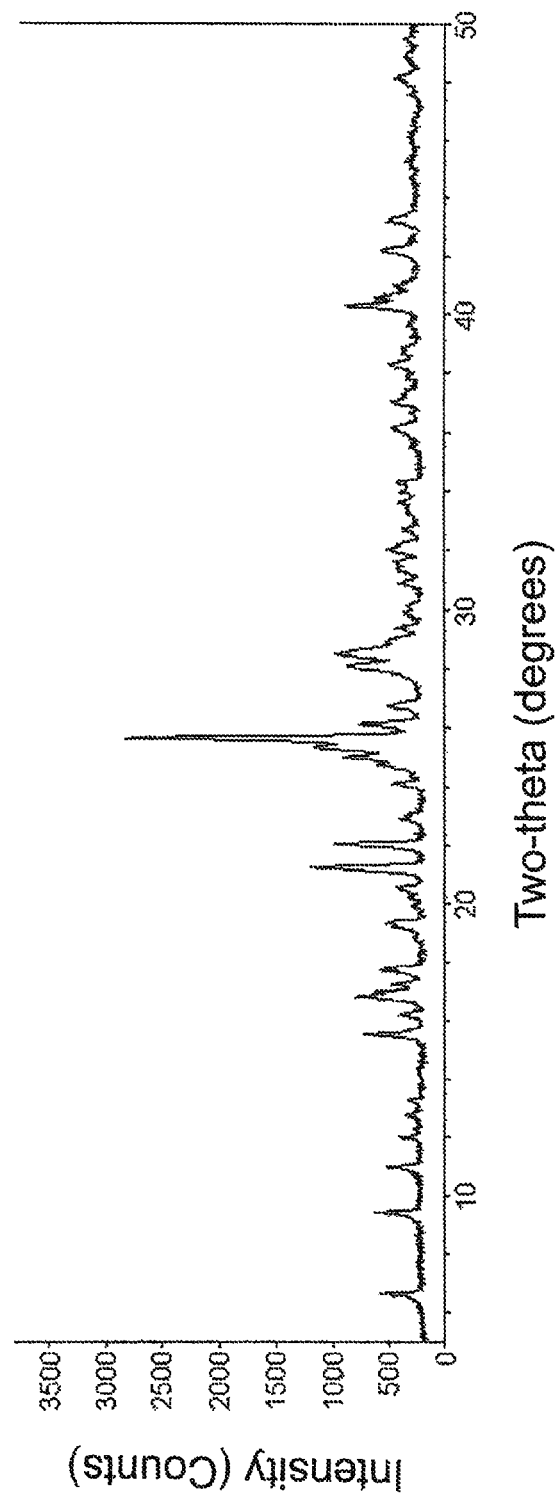
FIG. 1B shows room temperature Cu-Kα1 powder X-ray diffraction patterns of polymorph Form B of Compound 1 showing absolute X-ray intensity in counts graphed against 2θ reflection positions in degrees.

The powder X-ray diffraction pattern of polymorph Form B of Compound 1 is shown in FIG. 1B. The corresponding 2θ values are tabulated in Table 5 of Characterization Example 2. Polymorph Form B of Compound 1 can be identified by a room-temperature powder Cu(Kα1)-X-ray diffraction pattern having at least the 2θ reflection positions (in degrees)

| 2θ | 2θ |
|---|---|
| 6.654 | 21.225 |
| 9.41 | 22.012 |
| 10.983 | 25.638 |
| 11.986 | 28.545 |
| 15.513 | 40.244 |

Single crystal X-ray diffraction can be used to characterize polymorph Form B. A description of single crystal X-ray diffraction of polymorph Form B is provided in Characterization Example 4. Crystals of polymorph Form B have a triclinic unit cell and may exhibit a variety of morphologies with needle, acicular and blocky morphologies being most typical.

Polymorph Form B of Compound 1 can also be characterized by Differential Scanning calorimetry. DSC indicates the melting point of polymorph Form B is about 192° C. The details of a DSC experiment are provided in Characterization Example 8.

Pure Polymorph Form B can be prepared directly during the preparation of Compound 1 in toluene (as described in Preparation Example 2).

Compound 1 can also exist as an amorphous solid. The powder X-ray diffraction pattern (pXRD) for the amorphous form of Compound 1 shows a broad reflection pattern across the two-theta angle lacking distinct reflection signals and thus is readily distinguished from the pXRD patterns of crystalline forms of Compound 1. The amorphous solid form can be prepared by standard methods known in the art, such as evaporation to dryness of solutions containing Compound 1, by quick cooling of melted Compound 1, by spray drying a solution of Compound 1 or by freeze-drying a frozen solution containing Compound 1.

Compound 1 can be prepared by a variety of methods that are described generally in World Patent Publication WO 2011/017342.

The preparation of polymorph Form A of Compound 1 can be accomplished by a process wherein Compound 1 is prepared directly from its starting materials as described in Preparation Examples 1 and 3. Alternatively, polymorph Form A can be prepared by (A) combining its starting materials in the presence of a first solvent to form an intermediate solid form of Compound 1, (B) optionally separating the intermediate solid form of Compound 1, and then (C) contacting the intermediate solid form of Compound 1 with a second solvent to convert the intermediate solid form to the polymorph Form A. This method is exemplified by combining Preparation Example 2 (which describes formation of polymorph Form B) and Preparation Examples 4, 5, 6 or 7 (which describe the conversion of polymorph Form B to Form A in various solvents). Another alternative to prepare polymorph Form A is to skip step (B) in the above method and convert the intermediate solid form of Compound 1 in situ to the polymorph Form A (wherein the second solvent is the same as the first solvent) as described in Preparation Example 8.

An especially useful method to prepare Compound 1 is shown in Scheme 1. The method involves treating a compound of Formula 2 (wherein R is $C_1$-$C_4$ alkyl) with a hydroxide base in water and then removal of the water to form the compound of Formula 3. The compound of Formula 3 is treated with a chlorinating agent in the presence of a chlorinating solvent to make the compound of Formula 4. Alternatively the compound of Formula 4 can be directly prepared from a compound of Formula 2 (wherein R is H). The compound of Formula 4 is then treated with a compound of Formula 5 in the presence of a first solvent and base to form Compound 1. When the reaction is complete the mixture is treated with water to dissolve by-product salts and the aqueous slurry is filtered to isolate Compound 1. The resultant polymorph of Compound 1 is determined by the reaction conditions of the final condensation reaction.

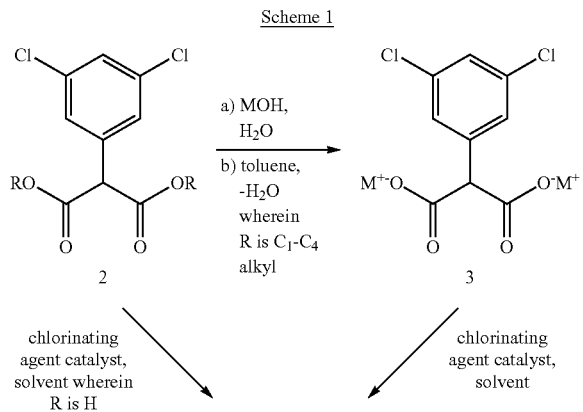

The compound of Formula 2 (wherein R is ethyl) is commercially available. The compound of Formula 2 (wherein R is H) can be prepared from compounds of Formula 2 (wherein R is $C_1$-$C_4$ alkyl) by methods well known in the art (see Preparation Example 3, Step B). Compounds of Formula 2 (wherein R is $C_1$-$C_4$ alkyl) can also be prepared by arylation of malonate esters with 1,3-dichloro-5-iodobenzene catalyzed by palladium (*J. Org. Chem.* 2002, 67, 541-555) or copper (*Org. Lett.* 2002, 4, 269-272 and *Org. Leu.* 2005, 7, 4693-4695). An example of the preparation of the compound of Formula 2 (wherein R is methyl) is described in Preparation Example 3, Step A.

The first step of Scheme 1 (conversion of a compound of Formula 2 to a compound of Formula 3) is a saponification reaction. An example of this procedure is described in Preparation Example 2, Step A. Saponification can take place with various bases, such as LiOH, NaOH, KOH, Ba(OH)$_2$, Ca(OH)$_2$, NH$_4$OH. Preferred for reasons of low cost are NaOH or KOH (M is Na or K in Formula 3). When the cation is in the +1 oxidation state, at least two equivalents of base are needed to convert both ester groups into carboxylate groups. When the cation is in the +2 oxidation state, at least one equivalent of base is needed to convert both ester groups into carboxylate groups. An excess of base is not deleterious to the reaction, and it may even be desirable to run the reaction with a small amount excess of base, ranging from about 0.02 to about 0.2 equivalents of base to the di-ester to ensure complete conversion of the more expensive di-ester of Formula 2.

The saponification can be performed at a temperature ranging from a low of about 0° C. or room temperature (about 25° C.) to a higher temperature of about 100° C. When the saponification is run at higher temperature, such as about 40° C. or above, side reactions such as decarboxylations can take place. It is most preferred to run the reaction at lower temperature, such as at room temperature. Because the saponification reaction is exothermic, it is desirable to control the rate of reaction, particularly when performing on a large scale. The rate of reaction can be controlled by either slow addition of compound of Formula 2 into the base solution, or by slow addition of the base into the mixture of compound of Formula 2 in water.

Preparation of a compound of Formula 3 can be performed in a co-solvent, such as an alcohol, an aromatic compound or an ether to facilitate the reaction. When a co-solvent is used a phase transfer catalyst, such as a tetrabutylammonium halide can also be employed to facilitate the hydrolysis. To eliminate the possibility of forming the partially decarboxylated side product (i.e. arylacetate), saponification of the malonate is best performed in water without a co-solvent or phase transfer catalyst. The arylacetate side product can not be easily removed during the isolation of a compound of Formula 3. Furthermore, this side product is not easily removed during the preparing the subsequent di-acid chloride of Formula 4, or preparation of the compound of Formula 1.

Isolation of the di-metal salt of Formula 3 is normally accomplished by removal of the solvent upon completion of the reaction. Removal of the solvent can be achieved by direct concentration of the saponification reaction mixture under vacuum. For example, the aqueous solution of di-metal salt can be concentrated directly to remove water. The resulting residue can be further triturated with an organic solvent, such as methanol, to isolate the di-metal salt compound (*Chem. Commun.* 2000, 1519-1520). This method frequently requires the reaction mixture to be heated to temperatures higher than ambient to temperature to promote the distillation of water. Since aqueous solutions of a compound of Formula 2 exhibit a higher rate of decomposition than the solid di-salts, an alternative procedure may be used. Excess water may be removed from the reaction mixture by slowly adding the reaction mixture into a heated organic solvent capable of rapidly distilling out water azeotropically. By running the distillation in this fashion, the aqueous solution will have minimal time to be exposed to high temperature.

Solvents appropriate to facilitate the removal by distillation of water for the present isolation method include aprotic solvents capable of forming a low-boiling azeotrope with water. The aprotic solvent is ordinarily a single solvent; it can also be a mixture of solvents such as xylene isomers. Low-boiling azeotropes usually have a boiling point less than both the boiling point of water and the boiling point of the solvent. By definition, low-boiling azeotropes containing water have normal boiling points of less than 100° C. (i.e. the normal boiling point of water). Thus the boiling point of the low-boiling azeotrope is substantially less than the boiling points of the compound of Formula 3, such that it will remain in the reaction mixture during distillation. As already mentioned, preferably the polar aprotic solvent and the aprotic solvent capable of forming a low-boiling azeotrope are selected so that the polar aprotic solvent has a boiling point higher than the azeotrope. The polar solvent is therefore not removed during the distillation. Solvents forming azeotropes with water are well known in the art, and compendia published listing their boiling points (see, for example, *Azeotropic Data*, Number 6 in the Advances in Chemistry Series, American Chemical Society, Washington, D.C., 1952, particularly pages 6-12). Examples of suitable aprotic solvents forming low-boiling azeotropes with water include esters such as ethyl acetate, butyl acetate and methyl butyrate; aromatic hydrocarbons such as benzene, toluene and xylenes; ethers such as tert-butyl methyl ether, tetrahydrofuran and 1,4-dioxane; alcohols such as isopropanol and propyl alcohol; and others such as acetonitrile and cyclohexane are suitable for the present method. Preferably, the azeotrope formed by the aprotic solvent and water contains a higher percentage of water than is soluble in the aprotic solvent at room temperature (e.g., 15-35° C.), thus facilitating large-scale separation of water from the condensed azeotrope in a decanter trap, and recycling the water-depleted aprotic solvent to the middle of the distillation column. Water-immiscible aprotic solvents such as ethyl acetate, benzene, toluene and tert-butyl methyl ether are preferred. The distillation can be run either at ambient atmosphere or at reduced pressure, such as 100 mmHg, which can easily be achieved in a manufacturing process. Distillation at reduced pressure speeds the distillation rate and lowers the boiling temperature and pot temperature. Lower pot temperature is beneficial because decarboxylation side reactions of compounds of Formula 3 are less likely.

The second step of Scheme 1 (conversion of a compound of Formula 3 to the compound of Formula 4) is a direct conversion of the di-salt to a di-acid chloride. An example of this procedure is described in Preparation Example 2, Step B. The conversion can be conducted with various halogenation reagents such as $COCl_2$, $ClC(O)OCCl_3$, $SOCl_2$, $(COCl)_2$, $POCl_3$, triphosgene and $PCl_5$. Thionyl chloride, (i.e. $SOCl_2$) can be used, however, oxalyl chloride (i.e. $(COCl)_2$) can be used with lower reaction temperatures (about 0° C. to about 30° C.) to affect the conversion. In order to convert one mole of the di-salt of Formula 3 to the corresponding di-acid chloride of Formula 4, the minimum required amount of halogenation reagent is two equivalents so as to convert both carboxylate di-salt groups into acid chloride groups. The reaction is usually run with an excess of halogenation reagent, from about 2.02 to about 3.0 equivalents of halogenating agent relative to the di-salt in order to ensure complete conversion of the compound of Formula 3.

The reaction can be run in the presence of a catalyst such as pyridine, N,N-dimethylformamide or 1-formylpiperidine, with a molar ratio of the catalyst to the compound of Formula 3 ranging from about 0.001 to about 0.4 or from about 0.005 to about 0.05. The reaction can be run in aprotic solvents such as toluene, dichloromethane, cyclohexane, benzene, 1,2-dichloroethane, ethyl acetate or butyl acetate, or a combination of these solvents. The reaction takes place at different temperatures depending on the chlorinating agent. When $(COCl)_2$ is used, the temperature ranges from about 0° C. to room temperature or from about 18° C. to about 30° C. When $SOCl_2$ is employed as the halogenating agent, a temperature of about 45° C. to about 80° C. can be used.

Combining a compound of Formula 3 with the halogenating agent can be accomplished in variety of ways. One method is to add a compound of Formula 3 as a solid (or as slurry in an appropriate solvent) into a solution of halogenation reagent in an aprotic solvent such as toluene, dichloromethane, cyclohexane, benzene, 1,2-dichloroethane, ethyl acetate or butyl acetate, or a combination of these solvents. The same or different solvents can be used to form the solution of halogenation reagent and slurry with a compound of Formula 3. This method keeps the compound of Formula 3 continuously exposed to halogenation reagent in large excess and is therefore halogenated as soon as the solid or slurry is added.

Alternatively a compound of Formula 4 can be prepared directly from a diacid of Formula 2 (wherein R is H) using the same halogenating reagents and the same reaction conditions as described above for the conversion of the disalt of Formula 3 into the diacid chloride of Formula 4. An example of this procedure is described in Preparation Example 3, Step C. Further examples of procedures can be found in Science of Synthesis, 20a-Product Class 1: acid halides, 2006, 15-52.

Although the conversion of di-salts to di-acid chlorides use similar reaction conditions as the conversion of di-acids to di-acid chlorides, the di-salt is converted directly to the corresponding diacid chloride without intermediate formation of the di-acid. The advantage of using the di-salts of Formula 3 is that only the corresponding metal chloride (for example NaCl or KCl) is generated as a reaction byproduct. This eliminates acidic reaction conditions which can be encountered during traditional conversion of di-acids into the corresponding di-acid chlorides with generation of hydrogen chloride as a reaction by-product. Di-acids of Formula 2 (wherein R is H) are susceptible to decarboxylation which can be difficult to prevent when handling the di-acids on a large scale.

The strong reactivity of di-acid chlorides towards relatively weak nucleophiles such as water requires that moisture be rigorously excluded when preparing, manipulating, or storing di-acid chlorides. The reaction should be conducted under dry nitrogen in dried solvents to obtain good yields. For the same reason, crude di-acid chloride solutions of Formula 4 should be used promptly with no purification in order to minimize the possibility of introducing moisture during manipulation or storage.

The third step of Scheme 1 is the condensation of the di-acid chloride (the compound of Formula 4 or 2-(3,5-dichlorophenyl)propanedioyl dichloride) with the amino substituted pyridine (the compound of Formula 5 or N-[(2-chloro-5-thiazolyl)methyl]-3-methyl-2-pyridinamine) in the presence of base to form Compound 1. Examples of this procedure are described in Preparation Examples 1 and 2, Step C or Preparation Example 3, Step D.

The stoichiometry of this reaction involves equimolar amounts of the compound of Formula 4 with a compound of Formula 5. However, small molar excesses of one of the reactants are not deleterious to the reaction. A slight excess (at most 1.10 molar equivalents or more typically 1.05 to 1.01 molar equivalents) of a compound of Formula 5 may be desirable to ensure complete conversion of the compound of Formula 4.

These reactions are typically performed in the presence of an acid acceptor. Typical acid acceptors include, but are not limited to, organic amines, such as trimethylamine, triethylamine, tributylamine, N,N-diisopropylethylamine, pyridine and substituted pyridines, metal oxides, such as calcium oxide, metal hydroxides such as sodium hydroxide and potassium hydroxide, metal carbonates, such as potassium carbonate and sodium carbonate, and metal bicarbonates, such as sodium bicarbonate or potassium bicarbonate. An especially useful acid acceptor is triethylamine.

The acid acceptor is added to the reaction mixture such that the molar ratio of acid acceptor to the compound of Formula 4 is typically in the range of about 1 to about 3. Typically a ratio in the range of about 2.0 to about 2.5 provides a rapid rate of reaction and high product yields.

The reaction to prepare Compound 1 is typically performed in an aprotic solvent, as protic solvents will react with the di-acid chloride of Formula 4. Typical solvents include hydrocarbons, chlorinated hydrocarbons, aromatic hydrocarbons, ethers, esters and nitriles. Solvents of note are xylenes, toluene, benzene, cyclohexane, dichloromethane, 1,2-dichloroethane, acetonitrile, ethyl acetate or butyl acetate, or a combination of these solvents. Toluene is an especially useful solvent for large scale preparation of Compound 1 because it is inert to the di-acid chloride, insoluble in water and easily recoverable.

The compounds of Formulae 4 and 5, the acid acceptor, and the aprotic solvent can be combined in any convenient order to form the reaction mixture. It is discovered that two mixing modes are particularly beneficial; the first being adding the acid acceptor slowly into the mixture of compounds of Formulae 4 and 5 to scavenge the hydrogen chloride by-product. The second mode of addition is to first prepare a mixture of a compound of Formula 5 and the acid acceptor, then slowly add a solution of a compound of Formula 4 to the resulting mixture. These two addition modes provide better control of the reaction rate and higher overall yield for the condensation.

Both the condensation reaction and the accompanying acid scavenging operation are exothermic, therefore cooling is necessary to remove excess heat generated, particularly at the beginning of each mixing operation when most heat is generated during a short period of time. The condensation reaction is typically conducted in a temperature range from about −10 to about 40° C. A particularly useful temperature range is from about 10 to 30° C. The initial condensation/acid scavenging reaction is typically not warmed above 40° C. because the compound of Formula 4 is subject to decomposition at elevated temperatures.

The condensation reaction to prepare Compound 1 is typically held at the designated temperature range for 30 minutes to about 8 hours. Reaction times are somewhat dependant on scale of the reaction with reaction times most typically in the range of about 1 to 4 hours.

Upon completion of the reaction, the reaction mixture is usually diluted with aqueous solutions to dissolve salts (triethylamine hydrochloride and sodium chloride) and reduce the solubility of the product, thus promoting the crystallization of product of high purity. The reaction mixture can be treated with a variety of aqueous solutions like aqueous sodium or potassium carbonate, 1N hydrochloric acid or neutral water. Another alternative is to exchange the reaction solvent for another as described in Preparation Example 1, Step C. Solvent exchange is sometimes desirable to replace a solvent with some water solubility (e.g. ethyl acetate) with a solvent with very little water solubility (e.g. toluene) to facilitate the dissolution of salts in the aqueous phase.

The reaction slurry is then cooled to a temperature in the range of 10 to 25° C. and filtered. The wet solid is washed with water, to remove traces of salts and washed with an organic solvent like ethyl acetate to displace water and higher boiling solvents (e.g. toluene) to facilitate drying. The separated solid or wet cake of Compound 1 can then be further isolated by drying or removing the last traces of solvent adhering to the external surface of the solid in a vacuum oven. The isolated solid can be characterized by a variety of analytical methods.

The condensation procedure yields polymorph Form A or polymorph Form B of Compound 1 depending on reaction conditions of solvent and temperature. At or near ambient temperature (about 20-30° C.) polymorph Form A is the condensation product in dichloromethane (see Preparation Example 3) and polymorph Form B is the condensation product in toluene (see Preparation Example 2). At higher temperatures (about 60-80° C.) polymorph Form A is the condensation product in ethyl acetate (see Preparation Example 1). If the initial condensation product is polymorph Form B it can be converted in situ to polymorph Form A by heating the reaction mixture (see Preparation Example 8). Isolated polymorph Form B of Compound 1 can be converted to the more thermodynamically stable polymorph Form A using a variety of solvents and temperatures as described in Preparation Examples 4, 5, 6 and 7.

The temperature of the conversion of polymorph Form B into polymorph Form A is dependant in part on the solubility of the starting solid forms of Compound 1 in the solvent. The polymorph form that results from the condensation reaction is also dependant in part on the temperature of the reaction and the solubility of Compound 1 in the solvent used for the reaction. The solvent and temperature range favoring a particular polymorph form cannot be predicted in advance. The relationships between temperature/solvent and polymorph form were experimentally determined and are shown in Table 3 of Preparation Example 6.

A variety of procedures can be used to prepare polymorph Form A of Compound 1. Selection of optimal procedures is typically based on a variety of factors, including the scale of the reaction. Performing the condensation at temperatures in the range of 20-30° C. provides mild reaction conditions reducing the decomposition of the di-acid chloride of Formula 4. Using moderately high boiling solvents such as toluene provides environmental benefits of reduced volatility while accommodating solvent recovery through distillation. Solvents having low water solubility, such as toluene, enable the removal of by-product triethylamine hydrochloride by partitioning it into an aqueous phase, thus facilitate isolation of Compound 1 with minimal contamination. Therefore particularly for large-scale preparations, choosing reaction conditions that are most suitable for the condensation reaction and which form polymorph Form B, and subsequently converting polymorph Form B to polymorph Form A may be most advantageous.

Seed crystals were used in some of the polymorph form interconversion procedures. Seed crystals are used to promote conversion and/or increase the rate of conversion of one polymorph into another. The polymorph conversion reactions are often agitated by a variety of methods even if not explicitly stated. The form of agitation can be from shaking the reaction vessel or by stirring with a magnetic or mechanical stirrer. The polymorph conversion reactions can also be agitated by the boiling action of the solvent.

The relative stability of polymorph Forms A and B of Compound 1 were studied. The two polymorph forms were subjected to non-competitive and competitive interconversion experiments. Characterization Examples 6 and 7 demonstrate that polymorph Form A is the more thermodynamically stable form at the temperatures used in the studies. Characterization Example 5 describes the heating of a sample of polymorph Form A and the monitoring of its powder X-ray diffraction pattern and verifies that Form A is the more thermodynamically stable form by the absence of a form-conversion. This study also indicates a monotropic relationship between polymorph Forms A and B, i.e. Form A is the thermodynamically more stable form over the entire temperature range from 25° C. to the melting point of Compound 1. Characterization Example 8 describes differential scanning calorimetry experiments for polymorph Forms A and B. From this study it may be concluded that the higher melting point of polymorph Form A compared to Form B indicates that Form A is more thermodynamically stable than Form B. The higher heat of fusion of Form A indicates a monotropic relationship between the two forms, i.e. Form A is thermodynamically more stable at any temperature below the melting temperature.

Polymorph Form A has physical properties that are more favorable for production than polymorph Form B. Increased crystal settling velocity is advantageous for separation by centrifugation and increased particle size is similarly advantageous for separation by filtration. Polymorph Form A can be more easily and efficiently separated from suspension by either means of solid-liquid separation (centrifugation or filtration), compared to Polymorph Form B. Polymorph Form A forms crystals with a larger average particle size than polymorph Form B which reduces dust associated with the handling of large quantities of material during commercial production. These favorable properties are evidenced in Characterization Examples 9, 10 and 11.

Without further elaboration, it is believed that one skilled in the art using the preceding description can utilize the present invention. The following Examples are, therefore, to be construed as merely illustrative, and not limiting of the disclosure in any way whatsoever. The starting material for the following Examples may not have necessarily been prepared by a particular preparative run whose procedure is described in other Examples. Abbreviations used in the examples are as follows: pXRD is powder X-ray diffraction, wt % is percent by weight measured by HPLC (using a calibration standard), a % is percent by area measured by HPLC at a wavelength of 230 nm and DSC is differential scanning calorimetry.

Analytical methods used in the preparation examples are described below or in the Characterization Examples.

High Performance Liquid Chromatography (HPLC)

HPLC was used to determine the purity of Compound 1 and intermediates. An Agilent 1100/1200 series HPLC system with DAD/UV detector and reverse-phase column (Agilent Zorbax® SB C8 (4.6×150) mm, 3.5 µm, Part No. 863953-906) was used. Flow rate was 1 mL/min, run time 27 min, injection volume 3.0 µL, and the column oven temperature was 40° C. A mobile phase gradient according to Table 1 was used wherein mobile phase A was 0.03% by volume orthophosphoric acid and mobile Phase B was acetonitrile (HPLC grade). Mobile phase A was prepared by thoroughly mixing 0.3 mL of orthophosphoric acid (AR grade) with 999.7 mL of deionized water. Standard solutions were prepared by weighing 22.0±2.0 mg of the analytical standard in duplicate into separate 50-mL volumetric flasks, dissolving and diluting with the diluent. Samples were prepared by weighing 40.0±2.0 mg of the sample into a 100 mL standard volumetric flask, dissolving and diluting with the diluent. For analysis, the HPLC system and column were equilibrated with initial mobile phase. In the chromatographic sequence, blank samples, standard samples and test samples were run. The retention time for Compound 1 was about 22.2 min. Peaks appearing in the blank sample were not integrated, all other peaks were integrated and a % purity reported from the sample chromatogram. For wt % determination the concentration of test sample was calibrated against the standard sample.

TABLE 1

Mobile Phase Gradient Table

| Time (min) | Volume Fraction of Mobile Phase A (%) | Volume Fraction of Mobile Phase B (%) |
|---|---|---|
| 0 | 85 | 15 |
| 18 | 50 | 50 |
| 24 | 0 | 100 |
| 27 | 0 | 100 |

Proton-Nuclear Magnetic Resonance ($^1$H-NMR)

Proton-NMR analysis was performed on a Bruker Advance 300/400 instrument. The operational frequency was 400 MHz, spectral frequency range 0-16 ppm, delay time 2 seconds, pulse width of 12 µs, minimum number of scans was 8. Samples were prepared by weighing about 0.01 g of samples or reference standards, adding 0.6 mL of DMSO-$d_6$ to dissolve the contents and transferring into NMR tubes. Deuterated DMSO (DMSO-$d_6$) was from Cambridge Isotope Labo-

PREPARATION EXAMPLE 1

Synthesis of Polymorph Form A of Compound 1 (Form A)

Step A: Preparation of Sodium 2-(3,5-dichlorophenyl)propanedioate (2:1)

The disodium salt of 2-(3,5-dichlorophenyl)propanedioate was prepared in a manner similar to that described for the potassium salt in Preparation Example 2, Step A.

Step B: Preparation of 2-(3,5-dichlorophenyl)propanedioyl Dichloride

An ice-water cooled mixture of oxalyl chloride (91.0 g, 717 mmol) in toluene (700 mL) under nitrogen was first treated with N,N-formylpiperidine (0.40 g, 3.58 mmol) and then sodium 2-(3,5-dichlorophenyl)propanedioate (2:1) (70 g, 239 mmol) was added in 7 batches of 10 g each at intervals of 15 min (gas evolution observed). A mild temperature rise was observed but the temperature was maintained at room temperature (23-25° C.) using an external ice-water bath. The cooling bath was removed after 30 min and the reaction mixture was stirred at room temperature for 4 h. The reaction mixture was then further warmed to 38-44° C. and stirred for one hour. After an hour, a vacuum was applied and the mixture was stirred under reduced pressure (92 mmHg) for 30 min to remove volatiles and any excess oxalyl chloride. A small volume of toluene (15 mL) distilled out. The resulting material was used directly in the next step.

Step C: Preparation of 1-[(2-chloro-5-thiazolyl)methyl]-3-(3,5-dichlorophenyl)-2-hydroxy-9-methyl-4-oxo-4H-pyrido[1,2-a]pyridinium Inner Salt (Compound 1)

The 2-(3,5-dichlorophenyl)propanedioyl dichloride mixture obtained in Step B above was cooled to 0° C. in an ice-water bath. A slurry of N-[(2-chloro-5-thiazolyl)methyl]-3-methyl-2-pyridinamine (57.27 g, 239 mmol) (prepared as in WO 2011/017342 Example 2, Step A) in EtOAc (700 mL) was added in 14 batches of 50 mL each at intervals of 5 min. The resulting mixture was stirred and allowed to warm to room temperature overnight. The reaction mixture was again cooled with an ice-water bath to 4° C. and a mixture of triethylamine (50.76 g, 502 mmol) in EtOAc (70 mL) was added dropwise over 30 min. A mild temperature rise was observed but the temperature was maintained under 11° C. After addition, the ice-water bath was removed and the mixture was stirred at room temperature for 3 h. The mixture was then heated to reflux for 3 h. After the 3 h period, EtOAc (700 mL collected) was slowly distilled out over another 3 h while toluene (700 mL) was added to replace the EtOAc. The resulting mixture was then cooled to room temperature overnight. The mixture was diluted with aqueous potassium carbonate (99 g, 717 mmol) in water (560 mL) and stirred for 40 min, filtered, and the resulting filter cake washed with water (2 times 280 mL) and ethyl acetate (2 times 280 mL). The wet cake was dried in a vacuum oven at 50° C. for 6 h to yield a dark yellow solid (87.76 g, 81.4%); melting point 205-206° C.

$^1$H NMR (CD$_3$COCD$_3$) δ 9.41-9.39 (m, 1H), 8.40-8.38 (m, 1H), 8.14-8.13 (m, 2H), 7.77 (s, 1H), 7.67-7.41 (m, 1H), 7.24-7.23 (m, 1H), 5.66 (s, 2H), 2.92 (s, 3H).

PREPARATION EXAMPLE 2

Synthesis of Polymorph Form B of Compound 1 (Form B)

Step A: Preparation of Potassium 2-(3,5-dichlorophenyl)propanedioate (2:1)

Potassium hydroxide (45% aqueous, 19 g, 152 7 mmol) was added to a stirred mixture of 1,3-dimethyl 2-(3,5-dichlorophenyl)propanedioate (20.0 g, 72.4 mmol) in water (40 mL) at 30° C. via a syringe pump over 2.5 h. A slight temperature increase to 30-35° C. was observed. The resulting white slurry/suspension turned into a clear solution over 3 h. The mixture was then stirred at room temperature for 16 h.

A Dean-Stark trap with condenser was fitted to a 500 mL round bottom flask containing toluene (300 mL). Toluene was stirred with heating to maintain a vigorous reflux (internal temperature of 125° C.). The aqueous solution of potassium 2-(3,5-dichlorophenyl)propanedioate (2:1) (total of 59 mL, as prepared above) was added via a syringe pump into the refluxing toluene over 2 h. The temperature cooled to 115° C. during the addition. Water (43.9 g) was collected and removed during the addition. The temperature (115° C.) was maintained for 1 h after the addition was complete and the mixture was cooled and stirred at room temperature for 16 h. Filtration of the cooled mixture gave a wet filter cake which was dried at 50° C. in a vacuum oven for 20 h to yield a fine white solid, (23.55 g, 98.6% after discounting 0.1 equivalents of potassium hydroxide) melting at 240-260° C. (dec.).

$^1$H NMR (CD$_3$COCD$_3$) δ 7.45-7.44 (m, 2H), 7.23-7.22 (m, 1H), 4.41 (s, 1H).

Step B: Preparation of 2-(3,5-dichlorophenyl)propanedioyl Dichloride

An ice-water cooled mixture of oxalyl chloride (13.76 g, 108 4 mmol) in toluene (100 mL) under nitrogen was first treated with N,N-dimethylformamide (6 drops) and then potassium 2-(3,5-dichlorophenyl)propanedioate (2:1) (11.60 g, 35.67 mmol) (a portion of the product of Step A) was added in 6 batches of 1.9 g each at intervals of 15 min (gas evolution observed). A mild temperature rise was observed but the temperature was maintained at room temperature (23-25° C.) using an external ice-water bath. The cooling bath was removed after 30 min and the reaction mixture was stirred at room temperature for 2 h. The mixture was then stirred under reduced pressure (20 mmHg) for 15 min to remove volatiles and any excess oxalyl chloride. The resulting material was used directly in the next step.

Step C: Preparation of 1-[(2-chloro-5-thiazolyl)methyl]-3-(3,5-dichlorophenyl)-2-hydroxy-9-methyl-4-oxo-4H-pyrido[1,2-a]pyridinium Inner Salt (Compound 1)

The 2-(3,5-dichlorophenyl)propanedioyl dichloride mixture obtained in Step B above was cooled to 0° C. in an ice-water bath. A slurry of N-[(2-chloro-5-thiazolyl)methyl]-3-methyl-2-pyridinamine (8.68 g, 36 2 mmol) (prepared as in WO 2011/017342 Example 2, Step A) in toluene (80 mL) was added over 20 min. The resulting mixture was stirred at 0° C. for 30 min, the ice-water bath was removed and stirring continued at room temperature for an additional 2 h. The reaction mixture was again cooled with an ice-water bath to 0° C. and a mixture of triethylamine (7.32 g, 72 3 mmol) in toluene (20 mL) was added dropwise over 30 min. A mild temperature rise was observed but the temperature was maintained at 23-30° C. using an external ice-water bath. The cooling bath was removed after the addition was complete and the reaction mixture was stirred at room temperature for 2 h. The mixture was diluted with water (80 mL), stirred for 30 min, filtered, and the resulting yellow filter cake washed with water (30 mL) and ethyl acetate (30 mL). The wet cake (19.9 g) was dried in a vacuum oven at 50° C. for 6 h to yield a yellow solid (14.58 g, 91.8%); melting point 190-191° C.

$^1$H NMR (CD$_3$COCD$_3$) δ 9.41-9.39 (m, 1H), 8.40-8.38 (m, 1H), 8.14-8.13 (m, 2H), 7.77 (s, 1H), 7.67-7.41 (m, 1H), 7.24-7.23 (m, 1H), 5.66 (s, 2H), 2.92 (s, 3H).

PREPARATION EXAMPLE 3

Synthesis of Polymorph Form A of Compound 1 (Form A)

Step A: Preparation of 1,3-dimethyl 2-(3,5-dichlorophenyl)propanedioate

A 1000-mL flask equipped with overhead stirrer, condenser and thermometer was charged with 1,3-dichloro-5-iodobenzene (99.0 g, 0.36 mol), 1,3-dimethyl 2-(3,5-dichlorophenyl)propanedioate (91.0 g, 0.69 mol), copper(I) iodide (4.0 g, 0.021mol), 2-picolinic acid (5.2 g, 0.042 mol) and cesium carbonate (350 g, 1.07 mol) in 1,4-dioxane (600 mL). The reaction mixture was heated under nitrogen to 90° C. for 3 hours. The mixture was then cooled to 30° C., diluted with water (300 mL) and hexane (200 mL), and partitioned. The organic phase was washed with saturated aqueous ammonium chloride solution (200 mL) and concentrated under vacuum to a viscous oil. The resulting material was used directly in the next step.

Step B: Preparation of 2-(3,5-dichlorophenyl)propanedioic Acid

The crude 1,3-dimethyl 2-(3,5-dichlorophenyl)propanedioate form Step A was taken up in methanol (150 mL) and water (300 mL). To this mixture was added 50% aqueous sodium hydroxide (120 g, 1.5 mol) over 30 min at room temperature. The reaction mixture was stirred at room temperature for 18 hours and then cooled to 10° C. in an ice bath. The mixture was acidified with concentrated hydrochloric acid (135 mL of 37%) over 30 min while maintaining the temperature of the reaction mixture at less than 17° C. The reaction mixture was extracted with ethyl acetate (600 mL) and the organic phase was concentrated under vacuum to give a viscous oil. The crude oil was treated with dichloromethane (200 mL) and stirred till a thick slurry formed. The slurry was filtered and dried via suction filtration under a nitrogen blanket for 48 hours at room temperature to give a solid (76.0 g, 84% over 2 steps).

$^1$H NMR (CD$_3$COCD$_3$) δ 11.64 (br s, 2H), 7.56 (s, 2H), 7.49 (s, 1H), 4.91 (s, 1H).

Step C: Preparation of 2-(3,5-dichlorophenyl)propanedioyl Dichloride

A 4-necked 500-mL flask equipped with overhead stirrer, condenser, thermometer, and addition funnel was charged with 2-(3,5-dichlorophenyl)propanedioic acid (21.8 g, 87.6 mmol), anhydrous dichloromethane (300 mL), and N,N-dimethylformamide (0.1 mL). To this stirred solution was added oxalyl chloride (19 mL, 217 mmol) over 10 min at room temperature. The mixture was stirred at room temperature for 1 hr, then refluxed for 2.5 h under nitrogen. The resulting yellow solution was concentrated under reduced pressure (20 mmHg) at a temperature of 25° C. to yield the crude product as an orange oil. The resulting material was used directly in the next step.

Step D: Preparation of 1-[(2-chloro-5-thiazolyl)methyl]-3-(3,5-dichlorophenyl)-2-hydroxy-9-methyl-4-oxo-4H-pyrido[1,2-a]pyridinium Inner Salt (Compound 1)

The 2-(3,5-dichlorophenyl)propanedioyl dichloride mixture obtained in Step B above was diluted with dichloromethane (200 mL) and cooled to 5° C. in an ice-water bath. To this solution was added N-[(2-chloro-5-thiazolyl)methyl]-3-methyl-2-pyridinamine (21 g. 87.6 mmol) (prepared as in WO 2011/017342 Example 2, Step A) in portions over 10 min. The resulting yellow slurry was stirred for 5 min in an ice bath, and then treated with triethylamine (12.0 mL, 86 mmol) dropwise over 15 min. The mixture was at 5° C. for additional 1 h. The resulting slurry was filtered, and the filter cake washed with cold (5° C.) dichloromethane (50 mL), 1N hydrochloric acid (50 mL x 2), and water (200 mL). The resulting solid was dried via suction filtration under a nitrogen blanket for 1 day to afford the product as a yellow crystalline solid (28.5 g, 72%); melting point 200-202° C.

$^1$H NMR (CD$_3$COCD$_3$) δ 9.41-9.39 (m, 1H), 8.40-8.38 (m, 1H), 8.14-8.13 (m, 2H), 7.77 (s, 1H), 7.67-7.41 (m, 1H), 7.24-7.23 (m, 1H), 5.66 (s, 2H), 2.92 (s, 3H).

PREPARATION EXAMPLE 4

Conversion of Polymorph Form B to Form A of Compound 1 Using Water and Toluene

Toluene and water were evaluated as solvents to convert polymorph Form B to Form A of Compound 1 with or without the use of seed crystals of Form A.

In Experiment 4a, a 100 mL three-neck round-bottom glass flask equipped with magnetic stirrer, oil bath, Dean-stark apparatus and temperature probe was charged with deionized water (20 mL) at 25° C. and then heated to 90° C. Polymorph Form B of Compound 1 (1 gram; polymorph form confirmed by pXRD) was added to the flask. The resultant slurry was further heated to 95° C. and stirred for about 5 hours. The slurry was then cooled to 28° C., stirred for 30 minutes and filtered. The filtered solids were dried in a tray dryer under vacuum at 50° C. for about 24 hours and analyzed by HPLC and pXRD. The X-ray diffractogram of the resulting sample indicated polymorph Form B of Compound 1.

In Experiment 4b, a 250 mL three-neck round-bottom glass flask equipped with an overhead stirrer, oil bath, Dean-Stark apparatus and temperature probe was charged with deionized water (50 mL) at 25° C. and then heated to 90° C. Polymorph Form B of Compound 1 (1 gram; polymorph form confirmed by pXRD) was added to the flask. The resultant slurry was further heated to 94° C. and stirred for 30 minutes. An additional 1 gram of Polymorph Form B of Compound 1 was then added. Seed crystals (about 20 mg) of polymorph Form A of Compound 1 were then added at 94° C. Heating and mixing was continued for about 5 hours. The slurry was cooled to 28° C., stirred for 30 minutes and filtered. The filtered solids were dried in a tray dryer under vacuum at 50° C. for about 24 hours and analyzed by HPLC and pXRD. The X-ray diffractogram of the resulting sample indicated polymorph Form A.

In Experiment 4c, a 100 mL three-neck round-bottom glass flask equipped with an overhead stirrer, oil bath and temperature probe was charged with 56 mL of toluene. Polymorph Form B of Compound 1 (3 grams; polymorph form confirmed by pXRD) was added to the flask at 25° C. The resultant slurry was heated and stirred at 106° C. Samples were withdrawn 2, 4 and 5 hours after commencement of heating. The heating was switched off after 6 hours. All slurry samples were cooled to 25° C. and filtered. The filtered solids were dried in under vacuum at 50° C. for 24 hours and analyzed by pXRD. The X-ray diffractograms of all resulting samples indicated polymorph Form A, i.e. the form conversion to Form A was complete 2 hours after commencement of heating.

In Experiment 4d, a 100 mL three-neck round-bottom glass flask equipped with an overhead stirrer, oil bath and temperature probe was charged with 56 mL of toluene. Polymorph Form B of Compound 1 (3 grams; polymorph form confirmed by pXRD) and polymorph Form A (0.1 gram; polymorph form confirmed by pXRD) were added to the flask at 25° C. The resultant slurry was heated and stirred at 106° C. Samples were withdrawn 2, 4 and 5 hours after commencement of heating. The heating was switched off after 6 hours. All slurry samples were cooled to 25° C. and filtered. The filtered solids were dried under vacuum at 50° C. for 24 hours and analyzed by pXRD. The X-ray diffractograms of all resulting samples indicated polymorph Form A, i.e. the form conversion to Form A was complete 2 hours after commencement of heating.

The results of Experiments 4a-d are summarized in Table 2 below.

TABLE 2

Polymorph form obtained by heating Form B of Compound 1 in water or toluene, with or without seeding with Form A

| Example | Heating time (hours) | Solvent; temperature (° C.) | Starting polymorph form(s) | Resulting polymorph form |
|---|---|---|---|---|
| 4a | 5 | Water; 95 | B | B |
| 4b | 5 | Water; 94 | B + seed A | A |
| 4c | 2, 4, 5, 6 | Toluene; 106 | B | A |
| 4d | 2, 4, 5, 6 | Toluene; 106 | B + seed A | A |

PREPARATION EXAMPLE 5

Conversion of Polymorph Form B to Form A of Compound 1 Using Toluene

A 250 ml three neck round bottom flask equipped with an over head stirrer, oil bath, and thermo probe was charged with polymorph Form B of 1-[(2-chloro-5-thiazolyl)methyl]-3-(3, 5-dichlorophenyl)-2-hydroxy-9-methyl-4-oxo-4H-pyrido[1, 2-a]pyridinium inner salt (Compound 1) (10.0 g, 22 mmol) and toluene (186 mL). The resultant slurry was heated to 106° C. and maintained for 2 hrs. The slurry was cooled to ambient temperature and stirred for 1 hr and then filtered. The filtered solid was suction dried for 1 hr and then dried in a vacuum oven at 50° C. for 24 hrs. The recovered yellow solid product (9.3 g, 93% yield) was analyzed by pXRD (polymorph Form A) and HPLC (99.0 wt % pure).

PREPARATION EXAMPLE 6

Conversion of Polymorph Form B of Compound 1 in Various Solvents

Form-conversion experiments were conducted with polymorph Form B of Compound 1 using a range of solvents and temperatures. Form B of Compound 1 was prepared as described in Preparation Example 2.

In each experiment, about 1 g of the polymorph Form B of Compound 1 was dispersed in 10 mL of the solvent in a the glass screw cap vial with magnetic stir bar. The mixture was then stirred at the target temperature for 24 hours. The mixture was then rapidly filtered through a syringe filter. The filtered solids were dried in a vacuum oven at 40° C. for about 24 hours and analyzed by pXRD. Table 3 below shows the obtained polymorph form by solvent type and temperature used.

TABLE 3

Polymorph form obtained by mixing Form B of Compound 1 in various solvents at temperatures between 20° C. and 80° C.

| Solvent | Resulting Polymorph Form | | | |
|---|---|---|---|---|
| | 20° C. | 40° C. | 60° C. | 80° C. |
| Tetrahydrofuran | A | A | A | — |
| Ethyl acetate | B | B | A | A |
| Methyl tert-butyl ether | B | B | — | — |
| Acetonitrile | A | A | A | A |
| 1,4-Dioxane | B | B | A | A |
| Methanol | B | A | — | — |
| Ethanol | B | B | A | — |
| Isopropyl alcohol | B | B | — | — |
| Dichloromethane | A | A | — | — |
| Acetone | A | A | — | — |
| Toluene | B | B | B | A |
| Water | B | B | B | B |
| Acetone/toluene (50:50 v/v) | A | A | — | — |

Notes:
'—' indicates "not determined".
'v/v' indicates "by volume"

PREPARATION EXAMPLE 7

Conversion of Polymorph Form B of Compound 1 Using Ethyl Acetate

A set of experiments was conducted to evaluate the conditions needed to convert polymorph From B of Compound 1 to Form A using ethyl acetate optionally mixed with water. The starting material of Compound 1 was prepared according to Preparation Example 2. Aliquots of Compound 1 thus prepared were slurried in ethyl acetate or a mixture of ethyl acetate with water under different conditions.

In Example 7a, about 1 g of polymorph From B of Compound 1 was stirred at about 60° C. with 10 mL of ethyl acetate for 3 hours, then filtered and vacuum dried at 40° C. for about 24 hours. Analysis by pXRD indicated polymorph Form B.

In Example 7b, about 1 g of polymorph From B of Compound 1 was stirred at about 60° C. with 10 mL of ethyl acetate for 15 hours, then filtered and vacuum dried at 40° C. for about 24 hours. Analysis by pXRD indicated polymorph Form A.

In Example 7c, about 1 g of polymorph From B of Compound 1 was stirred at about 72° C. with 10 mL of ethyl acetate. Samples were drawn after 2, 4, 6, 8 and 15 hours. The samples were filtered and vacuum dried at 40° C. for about 24 hours. Analysis by pXRD indicated polymorph Form B for the samples drawn after 2, 4 and 6 hours and polymorph Form A for the samples drawn after 8 and 15 hours.

In Example 7d, about 1 g of polymorph From B of Compound 1 was stirred at about 61° C. with 10 mL of ethyl acetate. Samples were drawn after 4 and 15 hours. The samples were filtered and vacuum dried at 40° C. for about 24 hours. Analysis by pXRD indicated polymorph Form A for both samples.

In Example 7e, about 1 g of polymorph From B of Compound 1 was stirred at about 61° C. with 6.6 mL of ethyl acetate and 3.3 mL of deionized water. Samples were drawn after 4 and 15 hours. The samples were filtered and vacuum dried at 40° C. for about 24 hours. Analysis by pXRD indicated polymorph Form A for both samples.

In Example 7f, about 1 g of polymorph From B of Compound 1 was stirred at about 72° C. with 6.6 mL of ethyl acetate and 3.3 mL of deionized water. Samples were drawn after 2 and 4 hours. The samples were filtered and vacuum dried at 40° C. for about 24 hours. Analysis by pXRD indicated polymorph Form A for both samples.

PREPARATION EXAMPLE 8

Synthesis of Polymorph Form A of Compound 1 (In Situ Conversion of Form B)

Step A: Preparation of 2-(3,5-dichlorophenyl)propanedioyl Dichloride

To an ice-water cooled mixture of oxalyl chloride (26.0 g, 204 7 mmol) in toluene (200 mL) under nitrogen was added N-formylpiperidine (0.12 g, 1.02 mmol). Sodium 2-(3,5-dichlorophenyl)propanedioate (2:1) (20 g, 68.3 mmol) was added in 4 batches of 5 g each at intervals of 15 min (gas evolution observed). A mild exotherm was observed but the temperature was maintained at 2-5° C. The cooling bath was removed 15 min after completion of the addition and the mixture was stirred at room temperature for 1.5 h. The reaction mixture was warmed to 48° C. and stirred for an additional 2 hours. Then vacuum (50 mmHg) was applied for 30 min to remove volatiles and any excess oxalyl chloride while some toluene (75 mL) distilled out. Fresh toluene (80 mL) was added to the resulting material and the crude solution was used directly in the next step.

Step B: Preparation of 1-[(2-chloro-5-thiazolyl)methyl]-3-(3,5-dichlorophenyl)-2-hydroxy-9-methyl-4-oxo-4H-pyrido[1,2-a]pyridinium Inner Salt (Compound 1)

The 2-(3,5-dichlorophenyl)propanedioyl dichloride mixture obtained in Step A above was cooled to 3° C. in an ice-water bath. A slurry of N-[(2-chloro-5-thiazolyl)methyl]-3-methyl-2-pyridinamine (16.36 g, 68.26 mmol) in toluene (180 mL) was added in 18 batches of 10 mL each at intervals of 3 min. The resulting mixture was stirred while warming over 18 hours. The reaction mixture was recooled with an ice-water bath to 4° C., and a mixture of triethylamine (13.81 g, 136.51 mmol) in toluene (70 mL) was added dropwise over 60 min. A mild exotherm was observed but the temperature was maintained under 5° C. After the addition was complete, the ice-water bath was removed and the mixture was stirred at room temperature for 18 hours. The resultant reaction mixture contains the title compound as polymorph Form B.

The mixture was then heated to reflux (112° C.) and maintained at that temperature for 6 hours. After about 4 hours at 112° C., the originally thick slurry turned into a slurry in which solid particles settled down easily when stirring was temporarily halted. The resulting mixture was then cooled to room temperature over 18 hours. The mixture was diluted with water (112 mL), stirred for 30 min, filtered, and the resulting filter cake was washed with water (2×60 mL) and ethyl acetete (2×60 mL). The wet cake was dried in a vacuum oven at 50° C. for 24 h to yield a yellow solid (24.07 g, 77.89%). DSC incated m.p. as 205.02° C., while X-Ray confirmed this material is polymorph Form A of Compound 1.

CHARACTERIZATION EXAMPLE 1

X-Ray Powder Diffraction for Compound 1 Polymorph Form A

Powder X-ray diffraction was used to identify the crystalline phases of various samples of Compound 1. Data were obtained with a Philips X'PERT automated powder diffractometer, Model 3040. The diffractometer was equipped with automatic variable anti-scatter and divergence slits, X'Celerator RTMS detector, and Ni filter. The radiation was Cu-K(alpha1) ($\lambda$=1.54059 Å) (45 kV, 40 mA). Data were collected at room temperature from 4 to 50 degrees 2-theta using a continuous scan with an equivalent step size of 0.02 degrees and a count time of 320 seconds per step in theta-theta geometry. Samples were lightly ground with an agate mortar and pestle as needed and prepared on low background silicon specimen holders as a thin layer of powdered material. MDI/Jade software version 9.1 is used with the International Committee for Diffraction Data database PDF4+ 2008 for phase identification. Diffraction maxima for Form A of Compound 1 were calculated using the MDI/Jade "Find Peaks" routine and are listed Table 4.

TABLE 4

2θ X-ray Maxima (in degrees) for Polymorph Form A of Compound 1

| 2θ |
|---|
| 8.036 |
| 9.592 |
| 12.866 |
| 13.719 |
| 14.453 |
| 15.822 |
| 16.025 |
| 17.07 |
| 18.248 |
| 19.301 |
| 19.902 |
| 22.893 |
| 23.092 |
| 23.336 |
| 24.027 |
| 24.481 |
| 24.987 |
| 25.316 |
| 25.951 |
| 26.267 |
| 26.805 |
| 27.419 |
| 27.705 |
| 28.19 |
| 28.923 |
| 29.743 |
| 31.353 |
| 31.831 |
| 33.868 |
| 36.287 |

TABLE 4-continued

2θ X-ray Maxima (in degrees) for Polymorph Form A of Compound 1

| 2θ |
|---|
| 37.077 |
| 37.517 |
| 37.947 |
| 39.15 |
| 39.439 |
| 40.451 |
| 40.975 |
| 42.011 |
| 42.401 |
| 42.528 |
| 43.912 |
| 46.247 |
| 49.143 |
| 49.609 |

CHARACTERIZATION EXAMPLE 2

X-Ray Powder Diffraction Pattern for Compound 1 Polymorph Form B

Powder X-ray diffraction was used to identify the crystalline phases of various samples of Compound 1. Data were obtained with a Philips X'PERT automated powder diffractometer, Model 3040. The diffractometer was equipped with automatic variable anti-scatter and divergence slits, X'Celerator RTMS detector, and Ni filter. The radiation was Cu-K(alpha1) ($\lambda$=1.54059 Å) (45 kV, 40 mA). Data were collected at room temperature from 4 to 50 degrees 2-theta using a continuous scan with an equivalent step size of 0.02 degrees and a count time of 320 seconds per step in theta-theta geometry. Samples were lightly ground with an agate mortar and pestle as needed and prepared on low background silicon specimen holders as a thin layer of powdered material. MDI/Jade software version 9.1 is used with the International Committee for Diffraction Data database PDF4+ 2008 for phase identification. Diffraction maxima for Form B of Compound 1 were calculated using the MDI/Jade "Find Peaks" routine and are listed Table 5.

TABLE 5

2θ X-ray Maxima (in degrees) for Polymorph Form B of Compound 1

| 2θ |
|---|
| 5.934 |
| 6.654 |
| 9.41 |
| 10.983 |
| 11.986 |
| 12.772 |
| 15.513 |
| 16.211 |
| 16.799 |
| 17.248 |
| 17.749 |
| 18.805 |
| 19.355 |
| 19.909 |
| 20.197 |
| 20.555 |
| 21.225 |
| 22.012 |
| 22.932 |
| 24.098 |
| 24.737 |
| 24.986 |
| 25.321 |
| 25.638 |
| 26.106 |
| 26.759 |
| 28.045 |
| 28.545 |
| 28.912 |
| 29.364 |
| 29.918 |
| 30.854 |
| 31.305 |
| 31.586 |
| 31.972 |
| 32.642 |
| 33.312 |
| 33.608 |
| 33.978 |
| 34.274 |
| 35.478 |
| 36.149 |
| 36.569 |
| 37.016 |
| 37.333 |
| 38.239 |
| 38.856 |
| 39.632 |
| 40.244 |
| 40.647 |
| 40.929 |
| 42.166 |
| 42.598 |
| 43.154 |
| 44.627 |
| 45.207 |
| 45.493 |
| 45.874 |
| 48.132 |
| 48.916 |
| 49.484 |

CHARACTERIZATION EXAMPLE 3

Single Crystal X-Ray Diffraction for Polymorph Form A of Compound 1

Suitable single crystals for polymorph Form A were grown from dichloromethane. A yellow needle with approximate dimensions of 0.550×0.160×0.140 mm was chosen for data collection and mounted on a polymer loop. Single crystal data was collected using a Bruker Platform goniometer with an Apex-II detector. The diffractometer was equipped with an incident beam monochromator using Mo-K$\alpha$ radiation ($\lambda$=0.71073 Å) and a monocap collimator. The crystals were cooled in a −100° C. nitrogen flow during data collection.

The data were indexed and integrated using the Apex-II suite of programs including Sainplus and SADABS. The monoclinic cell parameters were determined to be: a=7.199(5) Å, b=13.781(9) Å, c=18.441(12) Å, beta=92.773(11) °, volume=1828(2) Å$^3$. The space group was determined to be P2$_1$/c. The molecular weight was 452.73 g/mol giving a calculated density of 1.645 g/cm$^3$, and µ(Mo)=0.64 mm$^{-1}$ for Z=4. Data reduction led to 3079 unique data from a two-theta range=3.70 to 49.38°. Structure solution and refinements were performed using the Shelxtl program suite with refinement based on F$^2$ with scattering factors from Int. Tab. Vol C Tables 4.2.6.8 and 6.1.1.4. The final refinement statistics include a data/parameter ratio=10.23, goodness-of-fit on F$^2$=1.06, R indices[I>4sigma(I)]R1=0.0535, wR2=0.1288, R indices(all data) R1=0.0692, wR2=0.1369, max difference peak and hole=0.700 and −0.351 e/Å$^3$. The asymmetric unit contains one molecule. The atomic fractional coordinates(×10$^4$) and equivalent isotropic displacement parameters are listed in Tables 6 and 7. U(eq) is defined as one third of the trace of the orthogonalized Uij tensor. The estimated standard deviations are shown in parentheses.

TABLE 6

Atomic Coordinates (×10$^4$) and Equivalent Isotropic Displacement Parameters (A$^2$ × 10$^3$) for Compound 1 Polymorph Form A

| Atom | x | y | z | U(eq) |
|---|---|---|---|---|
| Cl(1) | 8176(2) | 9240(1) | 198(1) | 43(1) |
| Cl(2) | 2900(2) | 2138(1) | 2468(1) | 45(1) |
| Cl(3) | 2383(2) | 3812(1) | −160(1) | 68(1) |
| S(1) | 5084(1) | 8211(1) | 866(1) | 33(1) |
| O(1) | 2639(4) | 6799(2) | 1168(1) | 40(1) |
| O(2) | 557(4) | 5304(2) | 3253(1) | 35(1) |
| N(3) | 2174(4) | 7635(2) | 2192(2) | 28(1) |
| N(5) | 1639(4) | 6864(2) | 3276(2) | 29(1) |
| N(14) | 5536(5) | 10066(2) | 934(2) | 36(1) |
| C(1) | 1967(5) | 5865(3) | 2199(2) | 28(1) |
| C(2) | 2311(5) | 6735(2) | 1813(2) | 29(1) |
| C(4) | 2051(5) | 7711(3) | 2926(2) | 27(1) |
| C(6) | 1327(5) | 5922(3) | 2899(2) | 29(1) |
| C(7) | 2371(5) | 8559(3) | 3347(2) | 29(1) |
| C(8) | 2212(6) | 8482(3) | 4087(2) | 36(1) |
| C(9) | 1784(6) | 7620(3) | 4426(2) | 38(1) |
| C(10) | 1520(6) | 6828(3) | 4014(2) | 34(1) |
| C(11) | 1843(6) | 8466(3) | 1683(2) | 29(1) |
| C(12) | 3511(6) | 8879(3) | 1347(2) | 31(1) |
| C(13) | 3981(6) | 9827(3) | 1315(2) | 35(1) |
| C(15) | 6217(6) | 9272(3) | 688(2) | 34(1) |
| C(16) | 2944(7) | 9531(3) | 3055(2) | 34(1) |
| C(17) | 2129(5) | 4898(3) | 1847(2) | 29(1) |
| C(18) | 2365(5) | 4059(3) | 2260(2) | 30(1) |
| C(19) | 2629(5) | 3175(3) | 1935(2) | 33(1) |
| C(20) | 2677(6) | 3072(3) | 1191(2) | 38(1) |
| C(21) | 2416(6) | 3901(3) | 783(2) | 39(1) |
| C(22) | 2128(6) | 4802(3) | 1087(2) | 36(1) |

TABLE 7

Hydrogen Coordinates (×10$^4$) and Isotropic Displacement Parameters (A$^2$ × 10$^3$) for Compound 1 Polymorph Form A

| Atom | x | y | z | U(eq) |
|---|---|---|---|---|
| H(8) | 2500(60) | 9110(30) | 4350(20) | 42(11) |
| H(9) | 1690(60) | 7610(30) | 4980(20) | 40(11) |
| H(10) | 1120(60) | 6220(30) | 4230(20) | 49(13) |
| H(11) | 810(60) | 8200(30) | 1270(20) | 42(11) |
| H(11A) | 1260(50) | 8970(30) | 1925(19) | 26(10) |
| H(13) | 3400(60) | 10340(30) | 1520(20) | 38(11) |
| H(16) | 1950(60) | 9850(30) | 2860(20) | 37(12) |
| H(16A) | 3640(70) | 9930(40) | 3440(30) | 67(15) |
| H(16B) | 3980(60) | 9450(30) | 2700(20) | 48(12) |
| H(18) | 2280(60) | 4090(30) | 2760(20) | 50(13) |
| H(20) | 2940(50) | 2490(30) | 986(19) | 25(9) |
| H(22) | 1910(60) | 5340(30) | 780(20) | 47(12) |

CHARACTERIZATION EXAMPLE 4

Single Crystal X-Ray Diffraction for Polymorph Form B of Compound 1

Suitable single crystals of polymorph Form B of Compound 1 were grown from acetone. A yellow needle with approximate dimensions of 0.180×0.050×0.050 mm was chosen for data collection and mounted on a polymer loop. Single crystal data was collected using a Bruker Platform goniometer with an Apex-II detector. The diffractometer is equipped with an incident beam monochromator using Mo-Kα radiation (λ=0.71073 Å) and a monocap collimator. The crystals were cooled in a −100° C. nitrogen flow during data collection.

The data were indexed and integrated using the Apex-II suite of programs including Sainplus and SADABS. The triclinic cell parameters were determined to be: a=7.223(6) Å, b=9.697(8) Å, c=13.840(12) Å, alpha=82.464(14) °, beta=75.188(14) °, gamma=80.884(14) °, volume=921.2(13) Å$^3$. The space group was determined to be P-1. The molecular weight was 452.73 g/mol giving a calculated density of 1.632 g/cm$^3$, and μ(Mo)=0.63 mm$^{-1}$ for Z=2. Data reduction led to 3239 unique data from a two-theta range=4.28 to 52.54°. Structure solution and refinements were performed using the Shelxtl program suite with refinement based on F$^2$ with scattering factors from Int. Tab. Vol C Tables 4.2.6.8 and 6.1.1.4. The final refinement statistics include a data/parameter ratio=12.80, goodness-of-fit on F$^2$=1.02, R indices[I>4sigma (I)]R1=0.0720, wR2=0.1650, R indices(all data) R1=0.1513, wR2=0.2097, max difference peak and hole=0.468 and −0.468 e/A$^3$. The asymmetric unit contains one molecule. The atomic fractional coordinates (×10$^4$) and equivalent isotropic displacement parameters are listed in Tables 8 and 9. U(eq) is defined as one third of the trace of the orthogonalized Uij tensor. The estimated standard deviations are shown in parentheses.

TABLE 8

Atomic Coordinates (×10$^4$) and Equivalent Isotropic Displacement Parameters (A$^2$ × 10$^3$) for Compound 1 Polymorph Form B

| Atom | x | y | z | U(eq) |
|---|---|---|---|---|
| Cl(1) | 8065(3) | 9188(2) | 5621(2) | 54(1) |
| Cl(2) | 2300(3) | 5071(2) | 13892(1) | 40(1) |
| Cl(3) | 2894(3) | 10025(2) | 11624(2) | 47(1) |
| S(1) | 4793(3) | 8124(2) | 7190(2) | 34(1) |
| O(1) | 2051(7) | 7666(5) | 9032(4) | 36(1) |
| O(2) | 2696(8) | 3169(5) | 10808(4) | 39(1) |
| N(3) | 2120(8) | 5692(6) | 8306(4) | 24(1) |
| N(5) | 2299(8) | 3478(6) | 9190(4) | 25(1) |
| N(14) | 5064(9) | 8224(6) | 5279(4) | 38(2) |
| C(1) | 2515(9) | 5505(7) | 10058(5) | 24(2) |
| C(2) | 2205(9) | 6368(8) | 9154(5) | 29(2) |
| C(4) | 2230(10) | 4266(7) | 8304(5) | 26(2) |
| C(6) | 2517(9) | 4062(8) | 10112(5) | 27(2) |
| C(7) | 2414(9) | 3540(8) | 7446(5) | 28(2) |
| C(8) | 2275(10) | 2118(8) | 7602(6) | 34(2) |
| C(9) | 2097(11) | 1371(8) | 8532(6) | 36(2) |
| C(10) | 2177(10) | 2061(7) | 9323(6) | 30(2) |
| C(11) | 1468(10) | 6726(7) | 7512(5) | 30(2) |
| C(12) | 3081(10) | 7411(7) | 6816(6) | 32(2) |
| C(13) | 3456(11) | 7600(8) | 5789(6) | 39(2) |
| C(15) | 5926(11) | 8503(7) | 5948(5) | 31(2) |
| C(16) | 2757(12) | 4191(8) | 6384(6) | 43(2) |
| C(17) | 2625(9) | 6181(7) | 10946(5) | 26(2) |
| C(18) | 2539(9) | 5409(7) | 11882(5) | 26(2) |
| C(19) | 2521(9) | 6077(7) | 12719(5) | 25(2) |
| C(20) | 2621(10) | 7483(8) | 12681(6) | 31(2) |
| C(21) | 2765(10) | 8217(8) | 11748(6) | 33(2) |
| C(22) | 2805(9) | 7606(8) | 10878(5) | 28(2) |

TABLE 9

Hydrogen Coordinates (×10$^4$) and Isotropic Displacement Parameters (A$^2$ × 10$^3$) for Compound 1 Polymorph Form B

| Atom | x | y | z | U(eq) |
|---|---|---|---|---|
| H(8A) | 2303 | 1636 | 7042 | 41 |
| H(9A) | 1924 | 408 | 8623 | 43 |
| H(10A) | 2149 | 1559 | 9963 | 36 |

TABLE 9-continued

Hydrogen Coordinates (×10$^4$) and Isotropic Displacement Parameters
(A$^2$ × 10$^3$) for Compound 1 Polymorph Form B

| Atom | x | y | z | U(eq) |
|---|---|---|---|---|
| H(11A) | 856 | 6234 | 7117 | 36 |
| H(11B) | 480 | 7458 | 7841 | 36 |
| H(13A) | 2634 | 7311 | 5438 | 47 |
| H(16A) | 2856 | 3469 | 5934 | 64 |
| H(16B) | 3961 | 4612 | 6211 | 64 |
| H(16C) | 1679 | 4918 | 6313 | 64 |
| H(18A) | 2493 | 4427 | 11947 | 31 |
| H(20A) | 2593 | 7923 | 13259 | 37 |
| H(22B) | 2953 | 8155 | 10249 | 34 |

CHARACTERIZATION EXAMPLE 5

Temperature-dependent X-Ray Powder Diffraction for Polymorph Form A of Compound 1

To assess the stability of polymorph Form A of Compound 1 with respect to temperature, X-ray powder diffraction patterns were obtained while heating a sample of Form A from 25° C. to above its melting point. The measurement was conducted at the 5-IDD beam line at the Advanced Photon Source synchrotron located at the Argonne National Laboratory (Argonne, Ill., USA). A Differential-Scanning calorimeter (DSC, Model DSC600, Linkam Scientific Instruments, Tadworth, U.K.) was mounted in vertical orientation to allow insertion of the DSC into the X-ray beam. The DSC was positioned in the beam line to accept a 100-200 µm square beam under high vacuum. The standard quartz window was replaced with polyimide film (Kapton®, 8 µm thickness, DuPont, Wilmington, Del., USA). An internal thermocouple was installed for temperature recording. A circular charged couple device (CCD) detector (Model Mar165, 165 mm diameter, Marresearch GmbH, Norderstedt, Germany) was used to detect the X-rays scattered from the sample. The detector was equipped with an aluminum cone that covered the detector and extended 100 mm from the face of the detector. This cone was quipped with a beam stop support and 5×3 mm lead beam stop. The cone was continuously purged with helium to minimize air scattering.

A sample (~20 mg) of polymorph Form A of Compound 1 was loaded in low-mass aluminum pans with hermetically sealed lids (Model Tzero, TA Instruments, New Castle, Del., USA). A 5 mm pin punch was used to tamp the sample into place. The sample was slowly compressed using this pin punch to about 0.5 mm below the top of the pan. The lid was securely installed using a Tzero press with the appropriate mandrels. A small spring (3-4 coils of 215 p.m think stainless steel wire, 7 mm coil diameter) was utilized to mount and center the sample pan into the DSC.

The run parameters during the data collection were as follows. The temperature was increased linearly from 25° C. to 250° C. at a rate of 10° C. per minute, then decreased linearly from 250° C. to 25° C. at the same rate. The temperature was controlled using the Linkam CI93 temperature controller and LNP cooling pump. The data was collected using Linkam Linksys32 software. The X-ray data was collected simultaneously, but independently. The wavelength was tuned to 0.07293 nm. The CCD detector was set at high resolution, 79 p.m pixel size. The distance between sample and CCD detector was 115 mm. Exposure time was 0.1 seconds, the frame rate was 1 frame per 10 seconds. The X-ray system was controlled using Certified Scientific Software SPEC and APS EPICS. The data reduction was performed using macros written to work with the SPEC software to reduce the two-dimensional patterns from the detector to a standard one-dimensional pXRD pattern relating scattered X-ray intensity to the scattering angle. The one-dimensional pXRD files were converted to Jade® format to allow further analysis using MDI/Jade software version 9.1. For crystal form identification, the pXRD patterns of the test sample was compared to the single-crystal reference patterns of Forms A and B, respectively.

The pXRD patterns of the test sample of polymorph Form A of Compound 1 corresponded to Form A over the entire temperature range from 25° C. to the melting point, i.e. no crystal form conversion to another polymorph occurred.

Without any limitation by theory, the absence of a form-conversion upon heating of polymorph Form A indicates a monotropic relationship between polymorph Forms A and B, i.e. Form A is the thermodynamically more stable form over the entire temperature range from 25° C. to the melting point of Compound 1.

Upon cooling the sample from its melted state to room temperature, the sample remained amorphous. Accordingly, no X-ray diffraction pattern was obtained.

CHARACTERIZATION EXAMPLE 6

Relative Stability of Polymorph Forms A and B of Compound 1

Polymorph Forms A and B of Compound 1 were subjected to non-competitive and competitive interconversion experiments. For the non-competitive experiments, only a single starting crystal form was used to study the potential conversion to another more stable form. For the competitive experiments, polymorph Forms A and B were mixed together and studied for the potential conversion to the more thermodynamically stable form. The starting polymorph form(s) were mixed with various solvents for 5 days at 22° C., and then filtered. The filtrate was analyzed by HPLC to determine the solubility of Compound 1 in the test solvent. The solids were dried and analyzed by pXRD. The resulting polymorph forms and their solubilities in the test solvents are given in Table 10.

The experiments indicate that polymorph Form A is more thermodynamically stable than Form B as evidenced by the conversion of polymorph Form B to Form A.

In the case of the solvents acetone and tetrahydrofuran, the starting polymorph converted to polymorph Form A with or without seeding with Form A. In the case of the solvents toluene, ethyl acetate and water, the starting polymorph converted to polymorph Form A only when seed crystals of Form A were present.

Without any limitation by theory, it appears apparent that both the presence of seed crystal of polymorph form A as well as a solvent that provides higher solubility for Compound 1, increases the rate of conversion of Form B to Form A.

A detailed description of the individual experiments for Examples 6a to 6j is given below.

In Example 6a, Form B of Compound 1 (0.3 g) was mixed with acetone (5 g) at 22° C. for 5 days. The slurry was then filtered through a syringe filter (0.45 µm glass fiber, type Whatman GE Autovial) and dried in a vacuum oven at 40° C. for 48 hours. Analysis by pXRD indicated Form A of compound 1.

In Example 6b, Form B (0.3 g) and Form A (0.01 g) of Compound 1 were mixed with acetone (5 g) at 22° C. for 5 days. The slurry was then filtered through a syringe filter (0.45 µm glass fiber, type Whatman GE Autovial) and dried in a vacuum oven at 40° C. for 48 hours. Analysis by pXRD indicated Form A of Compound 1.

In Example 6c, Form B (0.3 g) of Compound 1 was mixed with tetrahydrofuran (5 g) at 22° C. for 5 days. The slurry was then filtered through a syringe filter (0.45 µm glass fiber, type Whatman GE Autovial) and dried in a vacuum oven at 40° C. for 48 hours. Analysis by pXRD indicated Form A of Compound 1.

In Example 6d, Form B (0.3 g) and Form A (0.01 g) of Compound 1 were mixed with tetrahydrofuran (5 g) at 22° C. for 5 days. The slurry was then filtered through a syringe filter (0.45 µm glass fiber, type Whatman GE Autovial) and dried in a vacuum oven at 40° C. for 48 hours. Analysis by pXRD indicated Form A of Compound 1.

In Example 6e, Form B (0.3 g) of Compound 1 was mixed with toluene (5 g) at 22° C. for 5 days. The slurry was then filtered through a syringe filter (0.45 µm glass fiber, type Whatman GE Autovial) and dried in a vacuum oven at 40° C. for 48 hours. Analysis by pXRD indicated Form B of Compound 1.

In Example 6f, Form B (0.3 g) and Form A (0.01 g) of Compound 1 were mixed with toluene (5 g) at 22° C. for 5 days. The slurry was then filtered through a syringe filter (0.45 µm glass fiber, type Whatman GE Autovial) and dried in a vacuum oven at 40° C. for 48 hours. Analysis by pXRD indicated Form A of Compound 1.

In Example 6g, Form B (0.3 g) of Compound 1 was mixed with ethyl acetate (5 g) at 22° C. for 5 days. The slurry was then filtered through a syringe filter (0.45 µm glass fiber, type Whatman GE Autovial) and dried in a vacuum oven at 40° C. for 48 hours. Analysis by pXRD indicated Form B of Compound 1.

In Example 6h, Form B (0.3 g) and Form A (0.01 g) of Compound 1 were mixed with ethyl acetate (5 g) at 22° C. for 5 days. The slurry was then filtered through a syringe filter (0.45 µm glass fiber, type Whatman GE Autovial) and dried in a vacuum oven at 40° C. for 48 hours. Analysis by pXRD indicated Form A of Compound 1.

In Example 6i, Form B (0.3 g) of Compound 1 was mixed with deionized water (5 g) at 22° C. for 5 days. The slurry was then filtered through a syringe filter (0.45 µm glass fiber, type Whatman GE Autovial) and dried in a vacuum oven at 40° C. for 48 hours. Analysis by pXRD indicated Form B of Compound 1.

In Example 6j, Form B (0.3 g) and Form A (0.01 g) of Compound 1 were mixed with deionized water (5 g) at 22° C. for 5 days. The slurry was then filtered through a syringe filter (0.45 µm glass fiber, type Whatman GE Autovial) and dried in a vacuum oven at 40° C. for 48 hours. Analysis by pXRD indicated Form A of Compound 1.

TABLE 10

Results of Relative Stability Experiments in Various Solvents at 22° C.

| Example | Solvent | Starting polymorph form(s) | Resulting polymorph form | Concentration of Compound 1 in filtrate (in wt %) |
| --- | --- | --- | --- | --- |
| 6a | Acetone | B | A | 0.34 |
| 6b | Acetone | B + seed A | A | 0.34 |
| 6c | Tetrahydrofuran | B | A | 1.03 |
| 6d | Tetrahydrofuran | B + seed A | A | 1.01 |
| 6e | Toluene | B | B | 0.049 |
| 6f | Toluene | B + seed A | A | 0.023 |
| 6g | Ethyl acetate | B | B | 0.18 |
| 6h | Ethyl acetate | B + seed A | A | 0.09 |
| 6i | Water | B | B | <0.01 |
| 6j | Water | B + seed A | A | <0.01 |

CHARACTERIZATION EXAMPLE 7

Relative Stability of Polymorph Forms A and B of Compound 1 at Elevated Temperature Polymorph Forms A and B of Compound 1 were subjected to competitive interconversion experiments. The starting polymorph Forms A and B were mixed in equal amounts in ethyl acetate (10 g of ethyl acetate per gram of Compound 1) at the desired temperature for about 48 hours, then filtered and dried. The dried solid was analyzed by pXRD. At both 40 and 60° C., as indicated in Table 11, polymorph Form A was obtained, indicating that polymorph Form A is the more thermodynamically stable form at the temperatures used.

TABLE 11

Results of Relative Stability Experiments at elevated temperature

| Example | Solvent | Mixing temperature (° C.) | Starting polymorph form(s) | Resulting polymorph form |
| --- | --- | --- | --- | --- |
| 7a | Ethyl acetate | 40 | A + B | A |
| 7b | Ethyl acetate | 60 | A + B | A |

CHARACTERIZATION EXAMPLE 8

Differential Scanning Calorimetry Experiments

The DSC thermogram for polymorph Form A of Compound 1 was observed to exhibit a sharp melting endotherm with an onset temperature at about 201° C., signal maximum at about 204° C. and a heat of fusion of 82-84 J/g.

The DSC thermogram for polymorph Form B of Compound 1 was observed to exhibit a sharp melting endotherm with an onset temperature of about 190° C., signal maximum at about 192° C. and a heat of fusion of about 65 J/g.

Table 12 below summarizes the DSC results for two separately prepared samples each of polymorph Form A and Form B, respectively.

Without any limitation by theory, it may be concluded that the higher melting point of polymorph Form A compared to Form B indicates that Form A is more thermodynamically stable than Form B. The higher heat of fusion of Form A indicates a monotropic relationship between the two forms, i.e. Form A is thermodynamically more stable at any temperature below the melting temperature. This follows from the heat of fusion rule (cf. e.g. R. Hilfiker (ed.), "Polymorphism in the Pharmaceutical Industry", 2006, Wiley-VCH, Weinheim, Germany).

TABLE 12

DSC Results for Polymorph Forms A and B of Compound 1

| Example | Polymorph Form | Fusion onset temp (° C.)/Fusion peak temp (° C.) | Heat of fusion (J/g) |
|---|---|---|---|
| 8a | A | 201/204 | 82 |
| 8b | A | 201/204 | 84 |
| 8c | B | 191/193 | 65 |
| 8d | B | 188/191 | 65 |

CHARACTERIZATION EXAMPLE 9

Solid-Liquid Separation Efficiency of Polymorph Forms A and B of Compound 1

The average particle size of Polymorph Form B of Compound 1 was observed to be consistently lower that Polymorph Form A. This can easily be observed during preparation of Polymorph Form A from Form B in a slurry form conversion experiment: When particles of Form B are suspended in a solvent the particles remain suspended when stirring is turned off. However, once Form B has converted to Form A in the slurry, the particles start to settle to the bottom of the flask rapidly after stirring is turned off indicating increased particle size of the Form A crystals. An increase in crystal density may also contribute to increased settling velocity; however the densities of the two polymorph form were found to be very similar (1.597 g/cm$^3$ for Form A and 1.582 g/cm$^3$ for Forms B, both measured by helium gas pygnometry). High particle size and settling velocities are important process advantages for solid-liquid separation operations in commercial manufacturing. Large average particle size improve filtration and centrifugation steps by increased filtration speeds, higher throughputs, lower propensity to filter cake cracking and resulting filtrate by-passing, increased cake wash efficiency and increased product purity.

In separate experiments, about 90 grams of Polymorph Forms A and B of Compound 1 were prepared according to PREPARATION EXAMPLE 1 and 2, respectively. The solids were filtered from their reaction mass using a lab nutsche filter. The times to complete the filtrations (indicated by no further liquid dripping from the filter) were measured and are reported in Table 12. The filtration time for Polymorph Form B was found to be more than 3 times longer than the filtration time for Polymorph Form A.

Hence, the filtration properties of Polymorph Form A are generally more desirable in the manufacturing process of Compound 1 than those of Polymorph Form B.

TABLE 12

Time required to complete filtration of 90 g of Polymorph Forms A and B of Compound 1

| Form | Filtration time |
|---|---|
| A | 0.9 min |
| B | 3.0 min |

CHARACTERIZATION EXAMPLE 10

Particle Size Distribution of Polymorph Forms A and B of Compound 1

After the observation of increased settling velocity of Polymorph Form A compared to Form B (see CHARACTERIZATION EXAMPLE 9), the particle size distributions of the two forms were measured. Form B of Compound 1 was prepared according to PREPARATION EXAMPLE 2. Some of the Form B thus prepared was converted to Form A according to PREPARATION EXAMPLE 5. The particle size distribution of both Form A and B samples were determined after dispersion in deionized water using a laser diffraction particle size analyzer (model Mastersizer 2000 by Malvern Instruments, Malvern, UK). The particle size distribution parameters D10, D50 and D90 are reported in Table 13 below, wherein D50 represents the median particle size of the distribution, i.e. 50% of the particles are smaller and 50% are larger than that size. D10 indicates the particle size at which 10% of all particles are smaller than that size. Similarly, D90 indicates the particle size at which 90% of all particles are smaller than that size. The volume-weighted mean particle sizes D[4,3] are also reported.

The particle size distribution of Polymorph Form A offers substantial industrial advantages compared to Form B. Those include increased solid-liquid separation efficiency for Form A using either filtration or centrifugation. Secondly, Form A provides improved handling properties in the solid state due to its substantial lack of a very fine particles fraction (below about 10 μm) resulting in less filter cloth blinding, less dusting, reduced worker exposure and cross-contamination in a multi-product production plant and reduced propensity to dust explosions.

TABLE 13

Particle size distribution parameters of Polymorph Forms A and B of Compound 1

| Form | D10 | D50 | D90 | D[4, 3] |
|---|---|---|---|---|
| A | 13 μm | 34 μm | 73 μm | 39 μm |
| B | 0.6 μm | 3.2 μm | 19 μm | 6.8 μm |

CHARACTERIZATION EXAMPLE 11

Increase of Crystal Settling Velocity During Conversion from Form B to Form A of Compound 1

This example illustrates that the increase of settling velocity coincides with the conversion of Polymorph Form B to Form A in a slurry of Compound 1.

Form B of Compound 1 was prepared according to PREPARATION EXAMPLE 2. Toluene (592 L) was charged to a clean stirred reactor (1000 liter glass-lined steel reactor) equipped with heating jacket and reflux condenser. Polymorph Form B of Compound 1 (39.4 kg) was then charged to the reactor at 25° C. The temperature was raised slowly until the temperature reached 103 to 106° C. The reaction temperature was then maintained between 103 to 106° C. (while returning condensed vapors to the reactor) for 6 hours. Slurry samples were withdrawn at the times indicated in Table 13, wherein time 0 indicates the time when the slurry temperature first reached 103° C. After each sample was taken the stirring was temporarily turned off to observe the settling of the crystals. No settling was observed for the times 0, 2.5 and 3.0 hours. Rapid settling of the crystals was observed for the times 3.5, 4.0 and 4.5 hours.

After 6 hours the reaction mass was cooled to 25° C. The solids were filtered and washed with toluene. The solids were suction dried on the filter and then dried in at 50-55° C. until the toluene content was below 0.3% by weight. The slurry samples taken during the experiment were also filtered and dried. The polymorph form of all dry samples was then analyzed by powder XRD (see Table 13).

As is apparent from Table 13, the conversion of Polymorph form B to form A coincides with an increase in settling velocity of the crystals.

TABLE 13

Settling behavior and Polymorph Form over the course of a crystal form conversion experiment

| Time (h) | Polymorph form* | Settling of crystals† |
|---|---|---|
| 0 | B | No settling observed |
| 2.5 | B | No settling observed |
| 3.0 | B | No settling observed |
| 3.5 | A | Rapid settling of crystals to bottom |
| 4.0 | A | Rapid settling of crystals to bottom |
| 4.5 | A | Rapid settling of crystals to bottom |
| After drying | A | Not applicable |

*by powder x-ray diffraction;
†after impeller temporarily turned off

Formulation/Utility

A solid form of Compound 1 will generally be used as a invertebrate pest control active ingredient in a composition, i.e. formulation, with at least one additional component selected from the group consisting of surfactants, solid diluents and liquid carriers (i.e. liquid fluids that carry the active and possibly other ingredients; also called liquid diluents). The formulation or composition ingredients are selected to be consistent with the physical properties of the active ingredient, mode of application and environmental factors such as soil type, moisture and temperature.

Useful formulations of invertebrate pest control active ingredients generally include both liquid and solid compositions. Liquid compositions include solutions (e.g., emulsifiable concentrates), emulsions (including micro-emulsions), dispersions and suspensions, and combinations of these forms (e.g., suspo-emulsions). The term "suspension" particularly refers to a dispersion of particulates that has been stabilized by addition of a chemical additive to minimize or stop sedimentation of the active ingredient. In a dispersion or suspension of particulates (e.g., aqueous suspension concentrate and oil dispersion formulations), a liquid carrier forms a continuous liquid phase in which the particulates (e.g., of a solid form of Compound 1) are dispersed or suspended. In a composition that combines a suspension or dispersion of particulates with an emulsion containing a second (immiscible) liquid (e.g., a suspo-emulsion formulation), a liquid carrier forms a continuous liquid phase in which not only the particulates are suspended but also droplets (i.e. non-continuous liquid phase) of the second liquid are emulsified.

Dispersions and suspensions may be aqueous (i.e. containing mainly water as the liquid carrier) or non-aqueous (i.e., comprising water-immiscible organic compounds, commonly referred to as "oil", as the liquid carrier) according to the nature of the liquid carrier forming the continuous liquid phase. The general types of aqueous liquid compositions include soluble concentrates, suspension concentrates, capsule suspensions, concentrated emulsions, micro-emulsions and suspo-emulsions. Thus in suspo-emulsions the liquid carrier forming the continuous liquid phase is aqueous (i.e. contains water as its main constituent) and a water-immiscible liquid component is emulsified in the aqueous liquid carrier. The general types of non-aqueous liquid compositions include emulsifiable concentrates, micro-emulsifiable concentrates, dispersible concentrates and oil dispersions. Suspension concentrates contain particulates dispersed in a continuous liquid phase and exists as particulate dispersions on addition to water. Suspo-emulsions and oil dispersions form both particulate dispersions and emulsions that coexist on addition to water, where one or more of these phases may contain active ingredient. (In the present compositions, the particulate dispersions comprise a solid form of Compound 1.)

The general types of solid compositions include dusts, powders, granules, pellets, prills, pastilles, tablets, filled films (including seed coatings) and the like, which can be water-dispersible ("wettable") or water-soluble. Films and coatings formed from film-forming liquids are particularly useful for seed treatment, in addition to having applications in both liquid and solid formulation types in general. Active ingredients can be encapsulated (including micro-encapsulated) and further formed into a liquid suspension or dispersion or into a solid formulation, to protect the active ingredient or control or delay release of the active ingredient on application to the target. Alternatively, the entire formulation, including the active ingredient, can be encapsulated (or "overcoated"). Encapsulation can also control or delay release of the active ingredient. High-strength compositions can be prepared and used as intermediates for subsequent use in preparing lower strength liquid and solid formulations.

Sprayable formulations are typically extended in a suitable medium before spraying. Such liquid and solid formulations are formulated to be readily diluted in the spray medium, usually water. Spray volumes can range from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

Although the solid forms of Compound 1 according to the present invention can be used to prepare liquid solutions, emulsifiable concentrates and emulsions by combining with a solvent dissolving the solid forms, the solid forms can only retain their identity in formulated compositions containing Compound 1 as a solid (e.g., particles). The invertebrate pest control compositions of the present invention wherein the composition comprises at least one solid form of Compound 1 thus include liquid compositions containing Compound 1 as a solid (e.g., dispersions, suspensions, suspo-emulsions) and solid compositions of Compound 1.

Even though all polymorph forms and the amorphous solid form of Compound 1 can be used to prepare invertebrate pest control compositions of the present invention, polymorph Form A is particularly useful for forming invertebrate pest control compositions, especially liquid compositions, having excellent physical as well as chemical stability. Although all polymorph forms and the amorphous solid form of Compound 1 are relatively stable (metastable) when isolated and maintained near room temperature, they are nevertheless thermodynamically unstable relative to polymorph Form A. Therefore, they are inherently susceptible to conversion to polymorph Form A. Contact with moisture, subjection to higher temperatures or long time periods may promote conversion to a more stable crystal form. Contact with solvents generally also promotes conversion of crystal forms. Therefore liquid compositions comprising other polymorph forms, mixtures of polymorph forms or the amorphous solid form of Compound 1 are particularly vulnerable to spontaneous recrystallization to polymorph Form A. Because of minimal nucleation and slow growth, the polymorph Form A crystals formed will be relatively few and large. This can result in both decreased biological efficacy and increased settling of the active ingredient, because high biological activity and suspensibility depend upon small particle size of solid active ingredient dispersed in liquid compositions. Using polymorph Form A to prepare invertebrate pest control compositions removes the risk of later recrystallization in the compositions. Also, a formulation containing a less stable crystal form than Form A may change its biological activity over the course of its shelf life as the ratio of crystal forms change. This is generally highly undesired as required use rates (amount of active ingredient per hectare) would change unpredictably. Accordingly, of note is a invertebrate pest control composition of the invention comprising polymorph Form A of Compound 1.

Both liquid and solid formulations comprising at least one solid form of Compound 1 will typically contain effective amounts of active ingredient, solid diluent or liquid carrier, and surfactant within the following approximate ranges, which add up to 100 percent by weight. General ranges of amounts of active ingredient (i.e. a solid form of Compound 1 and optionally other active ingredients), diluent and surfactant components in the present composition comprising at least one solid form of Compound 1 are as follows:

| | Composition in Weight Percent | | |
|---|---|---|---|
| Formulation Type | Active Ingredient | Diluent | Surfactant |
| Water-Dispersible Granules, Tablets and Powders | 0.001-90 | 0-99.999 | 0-25 |
| Oil Dispersions, Aqueous Suspensions | 1-60 | 40-99 | 0-50 |
| Dusts | 1-25 | 70-99 | 0-5 |
| Granules and Pellets | 0.001-95 | 5-99.999 | 0-20 |
| High Strength Compositions | 90-99 | 0-10 | 0-10 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, triacetin, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as simple quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic or pseudoplastic thickeners), in-container microbial growth (antimicrobials), product freezing (antifreezes), color (dyes/pigment dispersions), wash-off (film formers or sticking agents), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The solid forms of Compound 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2000 μm can be wet milled using media mills to obtain particles with average diameters below 3 μm. Aqueous slurries can be made into finished suspension concentrates (see, for example, U.S. Pat. No.3, 060,084) or further processed by spray-drying to form water-dispersible granules. Dry formulations usually require dry milling processes, which produce average particle diameters in the 2 to 10 μm range. Dusts and powders can be prepared by blending and grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pages 147-48; *Perry's Chemical Engineer's Handbook*, 4th Ed., McGraw-Hill, New York, 1963, pages 8-57 and following, and WO 91/13546. Pellets can be prepared as described in U.S. Pat. No. 4,172, 714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food—Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pages 81-96; Hance et al., *Weed Control Handbook*, 8th Ed., Blackwell Scientific Publications, Oxford, 1989; and *Developments in formulation technology*, PJB Publications, Richmond, UK, 2000.

The following formulation examples are presented to further illustrate but not limit the disclosure in any way whatsoever. All percentages are given by weight and all formulations are prepared using conventional techniques. Without further elaboration, it is believed that one skilled in the art using the preceding descriptions and references can utilize the present invention to its fullest extent.

FORMULATION EXAMPLE A

| High Strength Concentrate | |
|---|---|
| polymorph Form A of Compound 1 | 98.5% |
| silica aerogel | 0.5% |
| synthetic amorphous fine silica | 1.0% |

FORMULATION EXAMPLE B

| Wettable Powder | |
|---|---|
| polymorph Forms A and B of Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

FORMULATION EXAMPLE C

| Granule | |
|---|---|
| polymorph Form A of Compound 1 | 10.0% |
| attapulgite granules (low volatile matter, 0.71/0.30 mm; U.S.S. No. 25-50 sieves) | 90.0% |

FORMULATION EXAMPLE D

| Extruded Pellet | |
|---|---|
| polymorph Form A of Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

FORMULATION EXAMPLE E

| Emulsifiable Concentrate | |
|---|---|
| polymorph Forms A and B of Compound 1 | 10.0% |
| polyoxyethylene sorbitol hexoleate | 20.0% |
| $C_6$-$C_{10}$ fatty acid methyl ester | 70.0% |

FORMULATION EXAMPLE F

| Microemulsion | |
|---|---|
| polymorph Form A of Compound 1 | 5.0% |
| polyvinylpyrrolidone-vinyl acetate copolymer | 30.0% |
| alkylpolyglycoside | 30.0% |
| glyceryl monooleate | 15.0% |
| water | 20.0% |

FORMULATION EXAMPLE G

| Seed Treatment | |
|---|---|
| polymorph Form A of Compound 1 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

FORMULATION EXAMPLE H

| Fertilizer Stick | |
|---|---|
| polymorph Form A of Compound 1 | 2.50% |
| pyrrolidone-styrene copolymer | 4.80% |
| tristyrylphenyl 16-ethoxylate | 2.30% |
| talc | 0.80% |
| corn starch | 5.00% |
| Nitrophoska ® Permanent 15-9-15 slow-release fertilizer (BASF) | 36.00% |
| kaolin | 38.00% |
| water | 10.60% |

Solid forms of Compound 1 exhibit activity against a wide spectrum of invertebrate pests. These pests include invertebrates inhabiting a variety of environments such as, for example, plant foliage, roots, soil, harvested crops or other foodstuffs, building structures or animal integuments. These pests include, for example, invertebrates feeding on foliage (including leaves, stems, flowers and fruits), seeds, wood, textile fibers or animal blood or tissues, and thereby causing injury or damage to, for example, growing or stored agronomic crops, forests, greenhouse crops, ornamentals, nursery crops, stored foodstuffs or fiber products, or houses or other structures or their contents, or being harmful to animal health or public health. Those skilled in the art will appreciate that not all compounds are equally effective against all growth stages of all pests.

The solid forms of Compound 1 and their compositions are thus useful agronomically for protecting field crops from phytophagous invertebrate pests, and also non-agronomically for protecting other horticultural crops and plants from phytophagous invertebrate pests. This utility includes protecting crops and other plants (i.e. both agronomic and nonagronomic) that contain genetic material introduced by genetic engineering (i.e. transgenic) or modified by mutagenesis to provide advantageous traits. Examples of such traits include tolerance to herbicides, resistance to phytophagous pests (e.g., insects, mites, aphids, spiders, nematodes, snails, plant-pathogenic fungi, bacteria and viruses), improved plant growth, increased tolerance of adverse growing conditions such as high or low temperatures, low or high soil moisture, and high salinity, increased flowering or fruiting, greater harvest yields, more rapid maturation, higher quality and/or nutritional value of the harvested product, or improved storage or process properties of the harvested products. Transgenic plants can be modified to express multiple traits. Examples of plants containing traits provided by genetic engineering or mutagenesis include varieties of corn, cotton, soybean and potato expressing an insecticidal *Bacillus thuringiensis* toxin such as YIELD GARD®, KNOCKOUT®, STARLINK®, BOLLGARD®, NuCOTN® and NEWLEAF®, and herbicide-tolerant varieties of corn, cotton, soybean and rapeseed such as ROUNDUP READY®, LIBERTY LINK®, IMI®, STS® and CLEARFIELD®, as well as crops expressing N-acetyltransferase (GAT) to provide resistance to glyphosate herbicide, or crops containing the HRA gene providing resistance to herbicides inhibiting acetolactate synthase (ALS). The solid forms of Compound 1 and their compositions may interact synergistically with traits introduced by genetic engineering or modified by mutagenesis, thus enhancing phenotypic expression or effectiveness of the traits or increasing the parasitic nematode control effectiveness of the present compounds and compositions. In particular, the solid forms of Compound 1 and their compositions may interact synergistically with the phenotypic expression of proteins or other natural products toxic to invertebrate pests to provide greater-than-additive control of these pests.

Compositions of this invention can also optionally comprise plant nutrients, e.g., a fertilizer composition comprising at least one plant nutrient selected from nitrogen, phosphorus, potassium, sulfur, calcium, magnesium, iron, copper, boron, manganese, zinc, and molybdenum. Of note are compositions comprising at least one fertilizer composition comprising at least one plant nutrient selected from nitrogen, phosphorus, potassium, sulfur, calcium and magnesium. Compositions of the present invention which further comprise at least one plant nutrient can be in the form of liquids or solids. Of note are solid formulations in the form of granules, small sticks or tablets. Solid formulations comprising a fertilizer composition can be prepared by mixing the compound or composition of the present invention with the fertilizer composition together with formulating ingredients and then preparing the formulation by methods such as granulation or extrusion. Alternatively solid formulations can be prepared by spraying a solution or suspension of a compound or composition of the present invention in a volatile solvent onto a previous prepared fertilizer composition in the form of dimensionally stable mixtures, e.g., granules, small sticks or tablets, and then evaporating the solvent.

Examples of agronomic or nonagronomic invertebrate pests include eggs, larvae and adults of the order Lepidoptera, such as armyworms, cutworms, loopers, and heliothines in the family Noctuidae (e.g., pink stem borer (*Sesamia inferens* Walker), corn stalk borer (*Sesamia nonagrioides* Lefebvre), southern armyworm (*Spodoptera eridania* Cramer), fall armyworm (*Spodoptera fugiperda* J. E. Smith), beet armyworm (*Spodoptera exigua* Hübner), cotton leafworm (*Spodoptera littoralis* Boisduval), yellowstriped armyworm (*Spodoptera ornithogalli* Guenée), black cutworm (*Agrotis ipsilon* Hufnagel), velvetbean caterpillar (*Anticarsia gemmatalis* Hübner), green fruitworm (*Lithophane antennata* Walker), cabbage armyworm (*Barathra brassicae* Linnaeus), soybean looper (*Pseudoplusia includens* Walker), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworms (Pyralidae: Crambinae) such as sod worm (*Herpetogramma licarsisalis* Walker), sugarcane stem borer (*Chilo infuscatellus* Snellen), tomato small borer (*Neoleucinodes elegantalis* Guenée), green leafroller (*Cnaphalocerus medinalis*), grape leaffolder (*Desmia funeralis* Hübner), melon worm (*Diaphania nitidalis* Stoll), cabbage center grub (*Helluala hydralis* Guenée), yellow stem borer (*Scirpophaga incertulas* Walker), early shoot borer (*Scirpophaga infuscatellus* Snellen), white stem borer (*Scirpophaga innotata* Walker), top shoot borer (*Scirpophaga nivella* Fabricius), dark-headed rice borer (*Chilo polychrysus* Meyrick), cabbage cluster caterpillar (*Crocidolomia binotalis* English)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck), citrus false codling moth (*Cryptophlebia leucotreta* Meyrick), citrus borer (*Ecdytolopha aurantiana* Lima), redbanded leafroller (*Argyrotaenia velutinana* Walker), obliquebanded leafroller (*Choristoneura rosaceana* Harris), light brown apple moth (*Epiphyas postvittana* Walker), European grape berry moth (*Eupoecilia ambiguella* Hübner), apple bud moth (*Pandemis pyrusana* Kearfott), omnivorous leafroller (*Platynota stultana* Walsingham), barred fruit-tree tortrix (*Pandemis cerasana* Hübner), apple brown tortrix (*Pandemis heparana* Denis & Schiffermüller)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus), peach fruit borer (*Carposina niponensis* Walsingham), peach twig borer (*Anarsia lineatella* Zeller), potato tuberworm (*Phthorimaea operculella* Zeller), spotted teniform leafminer (*Lithocolletis blancardella* Fabricius), Asiatic apple leafminer (*Lithocolletis ringoniella* Matsumura), rice leaffolder (*Lerodea eufala* Edwards), apple leafminer (*Leucoptera scitella* Zeller)); eggs, nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella germanica* Linnaeus), brownbanded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)), smoky brown cockroach (*Periplaneta fuliginosa* Service), Australian Cockroach (*Periplaneta australasiae* Fabr.), lobster cockroach (*Nauphoeta cinerea* Olivier) and smooth cockroach (*Symploce pallens* Stephens)); eggs, foliar feeding, fruit feeding, root feeding, seed feeding and vesicular tissue feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus)), annual bluegrass weevil (*Listronotus maculicollis* Dietz), bluegrass billbug (*Sphenophorus parvulus* Gyllenhal), hunting billbug (*Sphenophorus venatus* vestitus), Denver billbug (*Sphenophorus cicatristriatus* Fahraeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte)); chafers and other beetles from the family Scarabaeidae (e.g., Japanese beetle (*Popillia japonica* Newman), oriental beetle (*Anomala orientalis* Waterhouse, *Exomala orientalis* (Waterhouse) Baraud), northern masked chafer (*Cyclocephala borealis* Arrow), southern masked chafer (*Cyclocephala immaculata* Olivier or *C. lurida* Bland), dung beetle and white grub (*Aphodius* spp.), black turfgrass ataenius (*Ataenius spretulus* Haldeman), green June beetle (*Cotinis nitida* Linnaeus), Asiatic garden beetle (*Maladera castanea* Arrow), May/June beetles (*Phyllophaga* spp.) and European chafer (*Rhizotrogus majalis* Razoumowsky)); carpet beetles from the family Dermestidae; wireworms from the family Elateridae; bark beetles from the family Scolytidae and flour beetles from the family Tenebrionidae.

In addition, agronomic and nonagronomic pests include: eggs, adults and larvae of the order Dermaptera including earwigs from the family Forficulidae (e.g., European earwig (*Forficula auricularia* Linnaeus), black earwig (*Chelisoches morio* Fabricius)); eggs, immatures, adults and nymphs of the orders Hemiptera and Homoptera such as, plant bugs from the family Miridae, cicadas from the family Cicadidae, leafhoppers (e.g. *Empoasca* spp.) from the family Cicadellidae, bed bugs (e.g., *Cimex lectularius* Linnaeus) from the family Cimicidae, planthoppers from the families Fulgoroidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, chinch bugs (e.g., hairy chinch bug (*Blissus leucopterus hirtus* Montandon) and southern chinch bug (*Blissus insularis* Barber)) and other seed bugs from the family Lygaeidae, spittlebugs from the family Cercopidae squash bugs from the family Coreidae, and red bugs and cotton stainers from the family Pyrrhocoridae.

Agronomic and nonagronomic pests also include: eggs, larvae, nymphs and adults of the order Acari (mites) such as spider mites and red mites in the family Tetranychidae (e.g., European red mite (*Panonychus ulmi* Koch), two spotted spider mite (*Tetranychus urticae* Koch), McDaniel mite (*Tetranychus mcdanieli* McGregor)); flat mites in the family Tenuipalpidae (e.g., citrus flat mite (*Brevipalpus lewisi* McGregor)); rust and bud mites in the family Eriophyidae and other foliar feeding mites and mites important in human and animal health, i.e. dust mites in the family Epidermoptidae, follicle mites in the family Demodicidae, grain mites in the family Glycyphagidae; ticks in the family Ixodidae, commonly known as hard ticks (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus)) and ticks in the family Argasidae, commonly known as soft ticks (e.g., relapsing fever tick (*Ornithodoros turicata*), common fowl tick (*Argas radiatus*)); scab and itch mites in the families Psoroptidae, Pyemotidae, and Sarcoptidae; eggs, adults and immatures of the order Orthoptera including grasshoppers, locusts and crickets (e.g., migratory grasshoppers (e.g., *Melanoplus sanguinipes* Fabricius, *M. differentialis* Thomas), American grasshoppers (e.g., *Schistocerca americana* Drury), desert locust (*Schistocerca gregaria* Forskal), migratory locust (*Locusta migratoria* Linnaeus), bush locust (*Zonocerus* spp.), house cricket (*Acheta domesticus* Linnaeus), mole crickets (e.g., tawny mole cricket (*Scapteriscus vicinus* Scudder) and southern mole cricket (*Scapteriscus borellii* Giglio-Tos)); eggs, adults and immatures of the order Diptera including leafminers (e.g., *Liriomyza* spp. such as serpentine vegetable leafminer (*Liriomyza sativae* Blanchard)), midges, fruit flies (Tephritidae), frit flies (e.g., *Oscinella* frit Linnaeus), soil maggots, house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; eggs, adults and immatures of the order Thysanoptera including onion thrips (*Thrips tabaci* Lindeman), flower thrips (*Frankliniella* spp.), and other foliar feeding thrips; insect pests of the order Hymenoptera including ants of the Family Formicidae including the Florida carpenter ant (Camponotus floridanus Buckley), red carpenter ant (*Camponotus ferrugineus* Fabricius), black carpenter ant (*Camponotus pennsylvanicus* De Geer), white-footed ant (*Technomyrmex albipes* fr. Smith), big headed ants (*Pheidole* sp.), ghost ant (Tapinoma melanocephalum Fabricius); Pharaoh ant (Monomorium pharaonis Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Forster) and odorous house ant (*Tapinoma sessile* Say). Other Hymenoptera including bees (including carpenter bees), hornets, yellow jackets, wasps, and sawflies (*Neodiprion* spp.; *Cephus* spp.); insect pests of the order Isoptera including termites in the Termitidae (e.g., *Macrotermes* sp., *Odontotermes obesus* Rambur), Kalotermitidae (e.g., *Cryptotermes* sp.), and Rhinotermitidae (e.g., *Reticulitermes* sp., *Coptotermes* sp., *Heterotermes tenuis* Hagen) families, the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder), powder post termite (*Cryptotermes brevis* Walker), drywood termite (*Incisitermes snyderi* Light), southeastern subterranean termite (*Reticulitermes virginicus* Banks), western drywood termite (*Incisitermes minor* Hagen), arboreal termites such as *Nasutitermes* sp. and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus capitis* De Geer), body louse (*Pediculus humanus* Linnaeus), chicken body louse (*Menacanthus stramineus* Nitszch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scutigera coleoptrata* Linnaeus).

Examples of invertebrate pests of stored grain include larger grain borer (*Prostephanus truncatus*), lesser grain borer (*Rhyzopertha dominica*), rice weevil (*Stiophilus oryzae*), maize weevil (*Stiophilus zeamais*), cowpea weevil (*Callosobruchus maculatus*), red flour beetle (*Tribolium castaneum*), granary weevil (*Stiophilus granarius*), Indian meal moth (*Plodia interpunctella*), Mediterranean flour beetle (*Ephestia kuhniella*) and flat or rusty grain beetle (*Cryptolestis ferrugineus*).

Solid forms of Compound 1 show particularly high activity against pests in the order Lepidoptera (e.g., *Alabama argillacea* Hübner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrosis medinalis* Guenée (rice leaf roller), *Crambus caliginosellus* Clemens (corn root webworm), *Crambus teterrellus* Zincken (bluegrass webworm), *Cydia pomonella* Linnaeus (codling moth), *Earias insulana* Boisduval (spiny bollworm), *Earias vittella* Fabricius (spotted bollworm), *Helicoverpa armigera* Hübner (American bollworm), *Helicoverpa zea* Boddie (corn earworm), *Heliothis virescens* Fabricius (tobacco budworm), *Herpetogramma licarsisalis* Walker (sod webworm), *Lobesia botrana* Denis & Schiffermüffler (grape berry moth), *Pectinophora gossypiella* Saunders (pink bollworm), *Phyllocnistis citrella* Stainton (citrus leafminer), *Pieris brassicae* Linnaeus (large white butterfly), *Pieris rapae* Linnaeus (small white butterfly), *Plutella xylostella* Linnaeus (diamondback moth), *Spodoptera exigua* Hübner (beet armyworm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tuta absoluta* Meyrick (tomato leafminer)).

Solid forms of Compound 1 also have significant activity on members from the order Homoptera including: *Acyrthosiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid),

*Dysaphis plantaginea* Paaserini (rosy apple aphid), *Eriosoma lanigerum* Hausmann (woolly apple aphid), *Hyalopterus pruni* Geoffroy (mealy plum aphid), *Lipaphis erysimi* Kaltenbach (turnip aphid), *Metopolophium dirrhodum* Walker (cereal aphid), *Macrosiphum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii* Boyer de Fonscolombe (black citrus aphid), and *Toxoptera citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly), *Bemisia argentifolii* Bellows & Perring (silverleaf whitefly), *Dialeurodes citri* Ashmead (citrus whitefly) and *Trialeurodes vaporariorum* Westwood (greenhouse whitefly); *Empoasca fabae* Harris (potato leafhopper), *Laodelphax striatellus* Fallen (smaller brown planthopper), *Macrolestes* quadrilineatus Forbes (aster leafhopper), *Nephotettix cinticeps* Uhler (green leafhopper), *Nephotettix nigropictus* Stal (rice leafhopper), *Nilaparvata lugens* Stal (brown planthopper), *Peregrinus maidis* Ashmead (corn planthopper), *Sogatella furcifera* Horvath (white-backed planthopper), *Sogatodes orizicola* Muir (rice delphacid), *Typhlocyba pomaria* McAtee white apple leafhopper, *Erythroneoura* spp. (grape leafhoppers); *Magicidada septendecim* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Trioza diospyri* Ashmead (persimmon psylla).

Compounds of this invention may also have activity on members from the order Hemiptera including: *Acrosternum hilare* Say (green stink bug), *Anasa tristis* De Geer (squash bug), *Blissus leucopterus leucopterus* Say (chinch bug), *Cimex lectularius* Linnaeus (bed bug) *Corythuca gossypii* Fabricius (cotton lace bug), *Cyrtopeltis modesta* Distant (tomato bug), *Dysdercus suturellus* Herrich-Schäffer (cotton stainer), *Euchistus servus* Say (brown stink bug), *Euchistus variolarius* Palisot de Beauvois (one-spotted stink bug), *Graptosthetus* spp. (complex of seed bugs), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* Dallas (large milkweed bug), *Pseudatomoscelis seriatus* Reuter (cotton fleahopper). Other insect orders controlled by solid forms of Compound 1 include Thysanoptera (e.g., *Frankliniella occidentalis* Pergande (western flower thrips), *Scirthothrips citri* Moulton (citrus thrips), *Sericothrips variabilis* Beach (soybean thrips), and *Thrips tabaci* Lindeman (onion thrips); and the order Coleoptera (e.g., *Leptinotarsa decemlineata* Say (Colorado potato beetle), *Epilachna varivestis* Mulsant (Mexican bean beetle) and wireworms of the genera *Agriotes, Athous* or *Limonius*).

Compounds of the present invention also have activity on members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and animal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala perfoliata* in horses, *Fasciola hepatica* Linnaeus in ruminants, etc.).

Note that some contemporary classification systems place Homoptera as a suborder within the order Hemiptera.

Of note is use of compounds of this invention for controlling potato leafhopper (*Empoasca fabae*). Of note is use of compounds of this invention for controlling corn planthopper (*Peregrinus maidis*). Of note is use of compounds of this invention for controlling cotton melon aphid (*Aphis gossypii*). Of note is use of compounds of this invention for controlling green peach aphid (*Myzus persicae*). Of note is use of compounds of this invention for controlling diamondback moth (*Plutella xylostella*). Of note is use of compounds of this invention for controlling fall armyworm (*Spodoptera frugiperda*).

Of note is use of compounds of this invention for controlling southern green stink bug (*Nezara viridula*), western tarnished plant bug (*Lygus hesperus*), rice water weevil (*Lissorhoptrus oryzophilus*), rice brown planthopper (*Nilaparvata lugens*), rice green leafhopper (*Nephotettix virescens*) and striped rice borer (*Chilo suppressalis*).

Solid forms of Compound 1 can also be mixed with one or more other biologically active compounds or agents including insecticides, fungicides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agronomic and nonagronomic utility. Thus the present invention also pertains to a composition comprising a solid form of Compound 1 and an effective amount of at least one additional biologically active compound or agent and can further comprise at least one of surfactants, solid diluents or liquid diluents. For mixtures of the present invention, the other biologically active compounds or agents can be formulated together with the solid forms of Compound 1, to form a premix, or the other biologically active compounds or agents can be formulated separately from the solid forms of Compound 1 and the two formulations combined together before application (e.g., in a spray tank) or, alternatively, applied in succession.

Examples of such biologically active compounds or agents with which solid forms of Compound 1 can be formulated are insecticides such as abamectin, acephate, acequinocyl, acetamiprid, acrinathrin, amidoflumet, amitraz, avermectin, azadirachtin, azinphos-methyl, bifenthrin, bifenazate, bistrifluron, borate, buprofezin, cadusafos, carbaryl, carbofuran, cartap, carzol, chlorantraniliprole, chlorfenapyr, chlorfluazuron, chlorpyrifos, chlorpyrifos-methyl, chromafenozide, clofentezin, clothianidin, cyantraniliprole, cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenothiocarb, fenoxycarb, fenpropathrin, fenvalerate, fipronil, flonicamid, flubendiamide, flucythrinate, flufenerim, flufenoxuron, fluvalinate, tau-fluvalinate, fonophos, formetanate, fosthiazate, halofenozide, hexaflumuron, hexythiazox, hydramethylnon, imidacloprid, indoxacarb, insecticidal soaps, isofenphos, lufenuron, malathion, metaflumizone, metaldehyde, methamidophos, methidathion, methiodicarb, methomyl, methoprene, methoxychlor, metofluthrin, monocrotophos, methoxyfenozide, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spirodiclofen, spiromesifen, spirotetramat, sulprofos, tebufenozide, tebufenpyrad, teflubenzuron, tefluthrin, terbufos, tetrachlorvinphos, tetramethrin, thiacloprid, thiamethoxam, thiodicarb, thiosultap-sodium, tolfenpyrad, tralomethrin, triazamate, trichlorfon, triflumuron, *Bacillus thuringiensis* delta-endotoxins, entomopathogenic bacteria, entomopathogenic viruses and entomopathogenic fungi.

Of note are insecticides such as abamectin, acetamiprid, acrinathrin, amitraz, avermectin, azadirachtin, bifenthrin, buprofezin, cadusafos, carbaryl, cartap, chlorantraniliprole, chlorfenapyr, chlorpyrifos, clothianidin, cyantraniliprole, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, flufenoxuron, fluvalinate, formetanate, fosthiazate, hexaflumuron, hydramethylnon, imidacloprid, indoxacarb, lufenuron, metaflumizone, methiodicarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, tebufenozide, tetramethrin, thiacloprid, thiamethoxam, thiodicarb, thiosultap-sodium, tralomethrin, triazamate, triflumuron, *Bacillus thuringiensis* delta-endotoxins, all strains of *Bacillus thuringiensis* and all strains of Nucleo polyhydrosis viruses.

One embodiment of biological agents for mixing with solid forms of Compound 1 include entomopathogenic bacteria such as *Bacillus thuringiensis*, and the encapsulated delta-endotoxins of *Bacillus thuringiensis* such as MVP® and MVPII® bioinsecticides prepared by the CellCap® process (CellCap®, MVP® and MVPII® are trademarks of Mycogen Corporation, Indianapolis, Ind., USA); entomopathogenic fungi such as green muscardine fungus; and entomopathogenic (both naturally occurring and genetically modified) viruses including baculovirus, nucleopolyhedro virus (NPV) such as *Helicoverpa zea* nucleopolyhedrovirus (HzNPV), *Anagrapha falcifera* nucleopolyhedrovirus (AfNPV); and granulosis virus (GV) such as *Cydia pomonella* granulosis virus (CpGV).

Of particular note is such a combination where the other invertebrate pest control active ingredient belongs to a different chemical class or has a different site of action than solid forms of Compound 1. In certain instances, a combination with at least one other invertebrate pest control active ingredient having a similar spectrum of control but a different site of action will be particularly advantageous for resistance management. Thus, a composition of the present invention can further comprise at least one additional invertebrate pest control active ingredient having a similar spectrum of control but belonging to a different chemical class or having a different site of action. These additional biologically active compounds or agents include, but are not limited to, sodium channel modulators such as bifenthrin, cypermethrin, cyhalothrin, lambda-cyhalothrin, cyfluthrin, beta-cyfluthrin, deltamethrin, dimefluthrin, esfenvalerate, fenvalerate, indoxacarb, metofluthrin, profluthrin, pyrethrin and tralomethrin; cholinesterase inhibitors such as chlorpyrifos, methomyl, oxamyl, thiodicarb and triazamate; neonicotinoids such as acetamiprid, clothianidin, dinotefuran, imidacloprid, nitenpyram, nithiazine, thiacloprid and thiamethoxam; insecticidal macrocyclic lactones such as spinetoram, spinosad, abamectin, avermectin and emamectin; GABA (γ-aminobutyric acid)-gated chloride channel antagonists such as avermectin or blockers such as ethiprole and fipronil; chitin synthesis inhibitors such as buprofezin, cyromazine, flufenoxuron, hexaflumuron, lufenuron, novaluron, noviflumuron and triflumuron; juvenile hormone mimics such as diofenolan, fenoxycarb, methoprene and pyriproxyfen; octopamine receptor ligands such as amitraz; molting inhibitors and ecdysone agonists such as azadirachtin, methoxyfenozide and tebufenozide; ryanodine receptor ligands such as ryanodine, anthranilic diamides such as chlorantraniliprole, cyantraniliprole and flubendiamide; nereistoxin analogs such as cartap; mitochondrial electron transport inhibitors such as chlorfenapyr, hydramethylnon and pyridaben; lipid biosynthesis inhibitors such as spirodiclofen and spiromesifen; cyclodiene insecticides such as dieldrin or endosulfan; pyrethroids; carbamates; insecticidal ureas; and biological agents including nucleopolyhedro viruses (NPV), members of *Bacillus thuringiensis*, encapsulated delta-endotoxins of *Bacillus thuringiensis*, and other naturally occurring or genetically modified insecticidal viruses.

Further examples of biologically active compounds or agents with which solid forms of Compound 1 can be formulated are: fungicides such as acibenzolar, aldimorph, amisulbrom, azaconazole, azoxystrobin, benalaxyl, benomyl, benthiavalicarb, benthiavalicarb-isopropyl, binomial, biphenyl, bitertanol, blasticidin-S, Bordeaux mixture (Tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflunamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, ethridiazole, famoxadone, fenamidone, fenarimol, fenbuconazole, fencaramid, fenfuram, fenhexamide, fenoxanil, fenpiclonil, fenpropidin, fenpropimorph, fentin acetate, fentin hydroxide, ferbam, ferfurazoate, ferimzone, fluazinam, fludioxonil, flumetover, fluopicolide, fluoxastrobin, fluquinconazole, fluquinconazole, flusilazole, flusulfamide, flutolanil, flutriafol, folpet, fosetyl-aluminum, fuberidazole, furalaxyl, furametapyr, hexaconazole, hymexazole, guazatine, imazalil, imibenconazole, iminoctadine, iodicarb, ipconazole, iprobenfos, iprodione, iprovalicarb, isoconazole, isoprothiolane, kasugamycin, kresoxim-methyl, mancozeb, mandipropamid, maneb, mapanipyrin, mefenoxam, mepronil, metalaxyl, metconazole, methasulfocarb, metiram, metominostrobin/fenominostrobin, mepanipyrim, metrafenone, miconazole, myclobutanil, neo-asozin (ferric methanearsonate), nuarimol, octhilinone, ofurace, orysastrobin, oxadixyl, oxolinic acid, oxpoconazole, oxycarboxin, paclobutrazol, penconazole, pencycuron, penthiopyrad, perfurazoate, phosphonic acid, phthalide, picobenzamid, picoxystrobin, polyoxin, probenazole, prochloraz, procymidone, propamocarb, propamocarb-hydrochloride, propiconazole, propineb, proquinazid, prothioconazole, pyraclostrobin, pryazophos, pyrifenox, pyrimethanil, pyrifenox, pyrolnitrine, pyroquilon, quinconazole, quinoxyfen, quintozene, silthiofam, simeconazole, spiroxamine, streptomycin, sulfur, tebuconazole, techrazene, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimoprhamide tricyclazole, trifloxystrobin, triforine, triticonazole, uniconazole, validamycin, vinclozolin, zineb, ziram, and zoxamide; nematocides such as aldicarb, imicyafos, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad.

In certain instances, combinations of solid forms of Compound 1 with other biologically active (particularly invertebrate pest control) compounds or agents (i.e. active ingredients) can result in a greater-than-additive (i.e. synergistic) effect. Reducing the quantity of active ingredients released in the environment while ensuring effective pest control is always desirable. When synergism with invertebrate pest control active ingredients occurs at application rates giving agronomically satisfactory levels of invertebrate pest control, such combinations can be advantageous for reducing crop production cost and decreasing environmental load.

Solid forms of Compound 1 and compositions thereof can be applied to plants genetically transformed to express proteins toxic to invertebrate pests (such as *Bacillus thuringiensis* delta-endotoxins). Such an application may provide a broader spectrum of plant protection and be advantageous for resistance management. The effect of the exogenously applied compounds of this invention may be synergistic with the expressed toxin proteins.

General references for these agricultural protectants (i.e. insecticides, fungicides, nematocides, acaricides, herbicides and biological agents) include The Pesticide Manual, 13th Edition, C. D. S. Tomlin, Ed., British Crop Protection Council, Farnham, Surrey, U.K., 2003 and The BioPesticide Manual, 2$^{nd}$ Edition, L. G. Copping, Ed., British Crop Protection Council, Farnham, Surrey, U.K., 2001.

For embodiments where one or more of these various mixing partners are used, the weight ratio of these various mixing partners (in total) to a solid form of Compound 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components can expand the spectrum of parasitic nematodes controlled beyond the spectrum controlled by a solid form of Compound 1 alone.

Table A lists specific combinations of a solid form of Compound 1 with other invertebrate pest control agents illustrative of the mixtures, compositions and methods of the present invention and includes additional embodiments of weight ratio ranges for application rates. The first column of Table A lists the specific invertebrate control agents (e.g., "Abamectin" in the first line). The second column of Table A lists the mode of action (if known) or chemical class of the invertebrate pest control agents. The third column of Table A lists embodiment(s) of ranges of weight ratios for rates at which the invertebrate pest control agent can be applied relative to a solid form of Compound 1 (e.g., "50:1 to 1:50" of abamectin relative to a solid form of Compound 1 by weight). Thus, for example, the first line of Table A specifically discloses the combination of a solid form of Compound 1 with abamectin can be applied in a weight ratio between 50:1 to 1:50. The remaining lines of Table A are to be construed similarly.

TABLE A

| Invertebrate Pest Control Agent | Mode of Action or Chemical Class | Typical Weight Ratio |
|---|---|---|
| Abamectin | macrocyclic lactones | 50:1 to 1:50 |
| Acetamiprid | neonicotinoids | 150:1 to 1:200 |
| Amitraz | octopamine receptor ligands | 200:1 to 1:100 |
| Avermectin | macrocyclic lactones | 50:1 to 1:50 |
| Azadirachtin | ecdysone agonists | 100:1 to 1:120 |
| Beta-cyfluthrin | sodium channel modulators | 150:1 to 1:200 |
| Bifenthrin | sodium channel modulators | 100:1 to 1:10 |
| Buprofezin | chitin synthesis inhibitors | 500:1 to 1:50 |
| Cartap | nereistoxin analogs | 100:1 to 1:200 |
| Chlorantraniliprole | ryanodine receptor ligands | 100:1 to 1:120 |
| Chlorfenapyr | mitochondrial electron transport inhibitors | 300:1 to 1:200 |
| Chlorpyrifos | cholinesterase inhibitors | 500:1 to 1:200 |
| Clothianidin | neonicotinoids | 100:1 to 1:400 |
| Cyantraniliprole | ryanodine receptor ligands | 100:1 to 1:120 |
| Cyfluthrin | sodium channel modulators | 150:1 to 1:200 |
| Cyhalothrin | sodium channel modulators | 150:1 to 1:200 |
| Cypermethrin | sodium channel modulators | 150:1 to 1:200 |
| Cyromazine | chitin synthesis inhibitors | 400:1 to 1:50 |
| Deltamethrin | sodium channel modulators | 50:1 to 1:400 |
| Dieldrin | cyclodiene insecticides | 200:1 to 1:100 |
| Dinotefuran | neonicotinoids | 150:1 to 1:200 |
| Diofenolan | molting inhibitor | 150:1 to 1:200 |
| Emamectin | macrocyclic lactones | 50:1 to 1:10 |
| Endosulfan | cyclodiene insecticides | 200:1 to 1:100 |
| Esfenvalerate | sodium channel modulators | 100:1 to 1:400 |
| Ethiprole | GABA-regulated chloride channel blockers | 200:1 to 1:100 |
| Fenothiocarb |  | 150:1 to 1:200 |
| Fenoxycarb | juvenile hormone mimics | 500:1 to 1:100 |
| Fenvalerate | sodium channel modulators | 150:1 to 1:200 |
| Fipronil | GABA-regulated chloride channel blockers | 150:1 to 1:100 |
| Flonicamid |  | 200:1 to 1:100 |
| Flubendiamide | ryanodine receptor ligands | 100:1 to 1:120 |
| Flufenoxuron | chitin synthesis inhibitors | 200:1 to 1:100 |
| Hexaflumuron | chitin synthesis inhibitors | 300:1 to 1:50 |
| Hydramethylnon | mitochondrial electron transport inhibitors | 150:1 to 1:250 |
| Imidacloprid | neonicotinoids | 1000:1 to 1:1000 |
| Indoxacarb | sodium channel modulators | 200:1 to 1:50 |
| Lambda-cyhalothrin | sodium channel modulators | 50:1 to 1:250 |
| Lufenuron | chitin synthesis inhibitors | 500:1 to 1:250 |
| Metaflumizone |  | 200:1 to 1:200 |
| Methomyl | cholinesterase inhibitors | 500:1 to 1:100 |
| Methoprene | juvenile hormone mimics | 500:1 to 1:100 |
| Methoxyfenozide | ecdysone agonists | 50:1 to 1:50 |
| Nitenpyram | neonicotinoids | 150:1 to 1:200 |
| Nithiazine | neonicotinoids | 150:1 to 1:200 |
| Novaluron | chitin synthesis inhibitors | 500:1 to 1:150 |
| Oxamyl | cholinesterase inhibitors | 200:1 to 1:200 |
| Pymetrozine |  | 200:1 to 1:100 |
| Pyrethrin | sodium channel modulators | 100:1 to 1:10 |
| Pyridaben | mitochondrial electron transport inhibitors | 200:1 to 1:100 |
| Pyridalyl |  | 200:1 to 1:100 |
| Pyriproxyfen | juvenile hormone mimics | 500:1 to 1:100 |
| Ryanodine | ryanodine receptor ligands | 100:1 to 1:120 |
| Spinetoram | macrocyclic lactones | 150:1 to 1:100 |
| Spinosad | macrocyclic lactones | 500:1 to 1:10 |
| Spirodiclofen | lipid biosynthesis inhibitors | 200:1 to 1:200 |
| Spiromesifen | lipid biosynthesis inhibitors | 200:1 to 1:200 |
| Tebufenozide | ecdysone agonists | 500:1 to 1:250 |
| Thiacloprid | neonicotinoids | 100:1 to 1:200 |
| Thiamethoxam | neonicotinoids | 1250:1 to 1:1000 |
| Thiodicarb | cholinesterase inhibitors | 500:1 to 1:400 |
| Thiosultap-sodium |  | 150:1 to 1:100 |
| Tralomethrin | sodium channel modulators | 150:1 to 1:200 |
| Triazamate | cholinesterase inhibitors | 250:1 to 1:100 |
| Triflumuron | chitin synthesis inhibitors | 200:1 to 1:100 |
| *Bacillus thuringiensis* | biological agents | 50:1 to 1:10 |
| *Bacillus thuringiensis* delta-endotoxin | biological agents | 50:1 to 1:10 |
| NPV (e.g., Gemstar) | biological agents | 50:1 to 1:10 |

Of note is the composition of the present invention wherein the at least one additional biologically active compound or agent is selected from the invertebrate pest control agents listed in Table A above.

The weight ratios of a solid form of Compound 1 to the additional invertebrate pest control agent typically are between 1000:1 and 1:1000, with one embodiment being between 500:1 and 1:500, another embodiment being between 250:1 and 1:200 and another embodiment being between 100:1 and 1:50.

Listed below in Table B are embodiments of specific compositions comprising a solid form of Compound 1 (polymorph Form A) and an additional invertebrate pest control agent.

TABLE B

| Mixture No. | Cmpd. 1 Form | and | Invertebrate Pest Control Agent | Typical Mixture Ratios (by weight) | | | | | | | |
|---|---|---|---|---|---|---|---|---|---|---|---|
| B-1 | A | and | Abamectin | 100:1 | 10:1 | 5:1 | 2:1 | 1:1 | 1:2 | 1:5 | 1:10 | 1:100 |
| B-2 | A | and | Acetamiprid | 100:1 | 10:1 | 5:1 | 2:1 | 1:1 | 1:2 | 1:5 | 1:10 | 1:100 |
| B-3 | A | and | Amitraz | 100:1 | 10:1 | 5:1 | 2:1 | 1:1 | 1:2 | 1:5 | 1:10 | 1:100 |
| B-4 | A | and | Avermectin | 100:1 | 10:1 | 5:1 | 2:1 | 1:1 | 1:2 | 1:5 | 1:10 | 1:100 |
| B-5 | A | and | Azadirachtin | 100:1 | 10:1 | 5:1 | 2:1 | 1:1 | 1:2 | 1:5 | 1:10 | 1:100 |
| B-5a | A | and | Bensultap | 100:1 | 10:1 | 5:1 | 2:1 | 1:1 | 1:2 | 1:5 | 1:10 | 1:100 |
| B-6 | A | and | Beta-cyfluthrin | 100:1 | 10:1 | 5:1 | 2:1 | 1:1 | 1:2 | 1:5 | 1:10 | 1:100 |
| B-7 | A | and | Bifenthrin | 100:1 | 10:1 | 5:1 | 2:1 | 1:1 | 1:2 | 1:5 | 1:10 | 1:100 |
| B-8 | A | and | Buprofezin | 100:1 | 10:1 | 5:1 | 2:1 | 1:1 | 1:2 | 1:5 | 1:10 | 1:100 |
| B-9 | A | and | Cartap | 100:1 | 10:1 | 5:1 | 2:1 | 1:1 | 1:2 | 1:5 | 1:10 | 1:100 |
| B-10 | A | and | Chlorantraniliprole | 100:1 | 10:1 | 5:1 | 2:1 | 1:1 | 1:2 | 1:5 | 1:10 | 1:100 |
| B-11 | A | and | Chlorfenapyr | 100:1 | 10:1 | 5:1 | 2:1 | 1:1 | 1:2 | 1:5 | 1:10 | 1:100 |
| B-12 | A | and | Chlorpyrifos | 100:1 | 10:1 | 5:1 | 2:1 | 1:1 | 1:2 | 1:5 | 1:10 | 1:100 |
| B-13 | A | and | Clothianidin | 100:1 | 10:1 | 5:1 | 2:1 | 1:1 | 1:2 | 1:5 | 1:10 | 1:100 |
| B-14 | A | and | Cyantraniliprole | 100:1 | 10:1 | 5:1 | 2:1 | 1:1 | 1:2 | 1:5 | 1:10 | 1:100 |
| B-15 | A | and | Cyfluthrin | 100:1 | 10:1 | 5:1 | 2:1 | 1:1 | 1:2 | 1:5 | 1:10 | 1:100 |
| B-16 | A | and | Cyhalothrin | 100:1 | 10:1 | 5:1 | 2:1 | 1:1 | 1:2 | 1:5 | 1:10 | 1:100 |
| B-17 | A | and | Cypermethrin | 100:1 | 10:1 | 5:1 | 2:1 | 1:1 | 1:2 | 1:5 | 1:10 | 1:100 |
| B-18 | A | and | Cyromazine | 100:1 | 10:1 | 5:1 | 2:1 | 1:1 | 1:2 | 1:5 | 1:10 | 1:100 |
| B-19 | A | and | Deltamethrin | 100:1 | 10:1 | 5:1 | 2:1 | 1:1 | 1:2 | 1:5 | 1:10 | 1:100 |
| B-20 | A | and | Dieldrin | 100:1 | 10:1 | 5:1 | 2:1 | 1:1 | 1:2 | 1:5 | 1:10 | 1:100 |
| B-21 | A | and | Dinotefuran | 100:1 | 10:1 | 5:1 | 2:1 | 1:1 | 1:2 | 1:5 | 1:10 | 1:100 |
| B-22 | A | and | Diofenolan | 100:1 | 10:1 | 5:1 | 2:1 | 1:1 | 1:2 | 1:5 | 1:10 | 1:100 |
| B-23 | A | and | Emamectin | 100:1 | 10:1 | 5:1 | 2:1 | 1:1 | 1:2 | 1:5 | 1:10 | 1:100 |
| B-24 | A | and | Endosulfan | 100:1 | 10:1 | 5:1 | 2:1 | 1:1 | 1:2 | 1:5 | 1:10 | 1:100 |
| B-25 | A | and | Esfenvalerate | 100:1 | 10:1 | 5:1 | 2:1 | 1:1 | 1:2 | 1:5 | 1:10 | 1:100 |
| B-26 | A | and | Ethiprole | 100:1 | 10:1 | 5:1 | 2:1 | 1:1 | 1:2 | 1:5 | 1:10 | 1:100 |
| B-27 | A | and | Fenothiocarb | 100:1 | 10:1 | 5:1 | 2:1 | 1:1 | 1:2 | 1:5 | 1:10 | 1:100 |
| B-28 | A | and | Fenoxycarb | 100:1 | 10:1 | 5:1 | 2:1 | 1:1 | 1:2 | 1:5 | 1:10 | 1:100 |
| B-29 | A | and | Fenvalerate | 100:1 | 10:1 | 5:1 | 2:1 | 1:1 | 1:2 | 1:5 | 1:10 | 1:100 |
| B-30 | A | and | Fipronil | 100:1 | 10:1 | 5:1 | 2:1 | 1:1 | 1:2 | 1:5 | 1:10 | 1:100 |
| B-31 | A | and | Flonicamid | 100:1 | 10:1 | 5:1 | 2:1 | 1:1 | 1:2 | 1:5 | 1:10 | 1:100 |
| B-32 | A | and | Flubendiamide | 100:1 | 10:1 | 5:1 | 2:1 | 1:1 | 1:2 | 1:5 | 1:10 | 1:100 |
| B-33 | A | and | Flufenoxuron | 100:1 | 10:1 | 5:1 | 2:1 | 1:1 | 1:2 | 1:5 | 1:10 | 1:100 |
| B-34 | A | and | Hexaflumuron | 100:1 | 10:1 | 5:1 | 2:1 | 1:1 | 1:2 | 1:5 | 1:10 | 1:100 |
| B-35 | A | and | Hydramethylnon | 100:1 | 10:1 | 5:1 | 2:1 | 1:1 | 1:2 | 1:5 | 1:10 | 1:100 |
| B-36 | A | and | Imidacloprid | 100:1 | 10:1 | 5:1 | 2:1 | 1:1 | 1:2 | 1:5 | 1:10 | 1:100 |
| B-37 | A | and | Indoxacarb | 100:1 | 10:1 | 5:1 | 2:1 | 1:1 | 1:2 | 1:5 | 1:10 | 1:100 |
| B-38 | A | and | Lambda-cyhalothrin | 100:1 | 10:1 | 5:1 | 2:1 | 1:1 | 1:2 | 1:5 | 1:10 | 1:100 |
| B-39 | A | and | Lufenuron | 100:1 | 10:1 | 5:1 | 2:1 | 1:1 | 1:2 | 1:5 | 1:10 | 1:100 |
| B-40 | A | and | Metaflumizone | 100:1 | 10:1 | 5:1 | 2:1 | 1:1 | 1:2 | 1:5 | 1:10 | 1:100 |
| B-41 | A | and | Methomyl | 100:1 | 10:1 | 5:1 | 2:1 | 1:1 | 1:2 | 1:5 | 1:10 | 1:100 |
| B-42 | A | and | Methoprene | 100:1 | 10:1 | 5:1 | 2:1 | 1:1 | 1:2 | 1:5 | 1:10 | 1:100 |
| B-43 | A | and | Methoxyfenozide | 100:1 | 10:1 | 5:1 | 2:1 | 1:1 | 1:2 | 1:5 | 1:10 | 1:100 |
| B-44 | A | and | Nitenpyram | 100:1 | 10:1 | 5:1 | 2:1 | 1:1 | 1:2 | 1:5 | 1:10 | 1:100 |
| B-45 | A | and | Nithiazine | 100:1 | 10:1 | 5:1 | 2:1 | 1:1 | 1:2 | 1:5 | 1:10 | 1:100 |
| B-46 | A | and | Novaluron | 100:1 | 10:1 | 5:1 | 2:1 | 1:1 | 1:2 | 1:5 | 1:10 | 1:100 |
| B-47 | A | and | Oxamyl | 100:1 | 10:1 | 5:1 | 2:1 | 1:1 | 1:2 | 1:5 | 1:10 | 1:100 |
| B-48 | A | and | Phosmet | 100:1 | 10:1 | 5:1 | 2:1 | 1:1 | 1:2 | 1:5 | 1:10 | 1:100 |
| B-49 | A | and | Pymetrozine | 100:1 | 10:1 | 5:1 | 2:1 | 1:1 | 1:2 | 1:5 | 1:10 | 1:100 |
| B-50 | A | and | Pyrethrin | 100:1 | 10:1 | 5:1 | 2:1 | 1:1 | 1:2 | 1:5 | 1:10 | 1:100 |
| B-51 | A | and | Pyridaben | 100:1 | 10:1 | 5:1 | 2:1 | 1:1 | 1:2 | 1:5 | 1:10 | 1:100 |
| B-52 | A | and | Pyridalyl | 100:1 | 10:1 | 5:1 | 2:1 | 1:1 | 1:2 | 1:5 | 1:10 | 1:100 |
| B-53 | A | and | Pyriproxyfen | 100:1 | 10:1 | 5:1 | 2:1 | 1:1 | 1:2 | 1:5 | 1:10 | 1:100 |
| B-54 | A | and | Ryanodine | 100:1 | 10:1 | 5:1 | 2:1 | 1:1 | 1:2 | 1:5 | 1:10 | 1:100 |
| B-55 | A | and | Spinetoram | 100:1 | 10:1 | 5:1 | 2:1 | 1:1 | 1:2 | 1:5 | 1:10 | 1:100 |
| B-56 | A | and | Spinosad | 100:1 | 10:1 | 5:1 | 2:1 | 1:1 | 1:2 | 1:5 | 1:10 | 1:100 |
| B-57 | A | and | Spirodiclofen | 100:1 | 10:1 | 5:1 | 2:1 | 1:1 | 1:2 | 1:5 | 1:10 | 1:100 |
| B-58 | A | and | Spiromesifen | 100:1 | 10:1 | 5:1 | 2:1 | 1:1 | 1:2 | 1:5 | 1:10 | 1:100 |
| B-59 | A | and | Spirotetramat | 100:1 | 10:1 | 5:1 | 2:1 | 1:1 | 1:2 | 1:5 | 1:10 | 1:100 |
| B-59a | A | and | Sulfoxaflor | 100:1 | 10:1 | 5:1 | 2:1 | 1:1 | 1:2 | 1:5 | 1:10 | 1:100 |
| B-60 | A | and | Tebufenozide | 100:1 | 10:1 | 5:1 | 2:1 | 1:1 | 1:2 | 1:5 | 1:10 | 1:100 |
| B-60a | A | and | Tefluthrin | 100:1 | 10:1 | 5:1 | 2:1 | 1:1 | 1:2 | 1:5 | 1:10 | 1:100 |
| B-61 | A | and | Thiacloprid | 100:1 | 10:1 | 5:1 | 2:1 | 1:1 | 1:2 | 1:5 | 1:10 | 1:100 |
| B-62 | A | and | Thiamethoxam | 100:1 | 10:1 | 5:1 | 2:1 | 1:1 | 1:2 | 1:5 | 1:10 | 1:100 |

TABLE B-continued

| Mixture No. | Cmpd. 1 Form | and | Invertebrate Pest Control Agent | Typical Mixture Ratios (by weight) | | | | | | | | |
|---|---|---|---|---|---|---|---|---|---|---|---|---|
| B-63 | A | and | Thiodicarb | 100:1 | 10:1 | 5:1 | 2:1 | 1:1 | 1:2 | 1:5 | 1:10 | 1:100 |
| B-64 | A | and | Thiosultap-sodium | 100:1 | 10:1 | 5:1 | 2:1 | 1:1 | 1:2 | 1:5 | 1:10 | 1:100 |
| B-65 | A | and | Tolfenpyrad | 100:1 | 10:1 | 5:1 | 2:1 | 1:1 | 1:2 | 1:5 | 1:10 | 1:100 |
| B-66 | A | and | Tralomethrin | 100:1 | 10:1 | 5:1 | 2:1 | 1:1 | 1:2 | 1:5 | 1:10 | 1:100 |
| B-67 | A | and | Triazamate | 100:1 | 10:1 | 5:1 | 2:1 | 1:1 | 1:2 | 1:5 | 1:10 | 1:100 |
| B-68 | A | and | Triflumuron | 100:1 | 10:1 | 5:1 | 2:1 | 1:1 | 1:2 | 1:5 | 1:10 | 1:100 |
| B-69 | A | and | *Bacillus thuringiensis* | 100:1 | 10:1 | 5:1 | 2:1 | 1:1 | 1:2 | 1:5 | 1:10 | 1:100 |
| B-70 | A | and | *Bacillus thuringiensis* delta-endotoxin | 100:1 | 10:1 | 5:1 | 2:1 | 1:1 | 1:2 | 1:5 | 1:10 | 1:100 |
| B-71 | A | and | NPV (e.g., Gemstar) | 100:1 | 10:1 | 5:1 | 2:1 | 1:1 | 1:2 | 1:5 | 1:10 | 1:100 |

Listed below in Table C are embodiments of specific compositions comprising a solid form of Compound 1 (polymorph Form A) and an additional fungicide.

TABLE C

| Mixture No. | Cmpd. 1 Form | and | Fungicide | Typical Mixture Ratios (by weight) | | | | | | | | |
|---|---|---|---|---|---|---|---|---|---|---|---|---|
| C-1 | A | and | Probenazole | 100:1 | 10:1 | 5:1 | 2:1 | 1:1 | 1:2 | 1:5 | 1:10 | 1:100 |
| C-2 | A | and | Tiadinil | 100:1 | 10:1 | 5:1 | 2:1 | 1:1 | 1:2 | 1:5 | 1:10 | 1:100 |
| C-3 | A | and | Isotianil | 100:1 | 10:1 | 5:1 | 2:1 | 1:1 | 1:2 | 1:5 | 1:10 | 1:100 |
| C-4 | A | and | Pyroquilon | 100:1 | 10:1 | 5:1 | 2:1 | 1:1 | 1:2 | 1:5 | 1:10 | 1:100 |
| C-5 | A | and | Metominostrobin | 100:1 | 10:1 | 5:1 | 2:1 | 1:1 | 1:2 | 1:5 | 1:10 | 1:100 |
| C-6 | A | and | Flutolanil | 100:1 | 10:1 | 5:1 | 2:1 | 1:1 | 1:2 | 1:5 | 1:10 | 1:100 |
| C-7 | A | and | Validamycin | 100:1 | 10:1 | 5:1 | 2:1 | 1:1 | 1:2 | 1:5 | 1:10 | 1:100 |
| C-8 | A | and | Furametpyr | 100:1 | 10:1 | 5:1 | 2:1 | 1:1 | 1:2 | 1:5 | 1:10 | 1:100 |
| C-9 | A | and | Pencycuron | 100:1 | 10:1 | 5:1 | 2:1 | 1:1 | 1:2 | 1:5 | 1:10 | 1:100 |
| C-10 | A | and | Simeconazole | 100:1 | 10:1 | 5:1 | 2:1 | 1:1 | 1:2 | 1:5 | 1:10 | 1:100 |
| C-11 | A | and | Orysastrobin | 100:1 | 10:1 | 5:1 | 2:1 | 1:1 | 1:2 | 1:5 | 1:10 | 1:100 |
| C-12 | A | and | Trifloxystrobin | 100:1 | 10:1 | 5:1 | 2:1 | 1:1 | 1:2 | 1:5 | 1:10 | 1:100 |
| C-13 | A | and | Isoprothiolane | 100:1 | 10:1 | 5:1 | 2:1 | 1:1 | 1:2 | 1:5 | 1:10 | 1:100 |
| C-14 | A | and | Azoxystrobin | 100:1 | 10:1 | 5:1 | 2:1 | 1:1 | 1:2 | 1:5 | 1:10 | 1:100 |
| C-15 | A | and | Tricyclazole | 100:1 | 10:1 | 5:1 | 2:1 | 1:1 | 1:2 | 1:5 | 1:10 | 1:100 |
| C-16 | A | and | Hexaconazole | 100:1 | 10:1 | 5:1 | 2:1 | 1:1 | 1:2 | 1:5 | 1:10 | 1:100 |
| C-17 | A | and | Difenoconazole | 100:1 | 10:1 | 5:1 | 2:1 | 1:1 | 1:2 | 1:5 | 1:10 | 1:100 |
| C-18 | A | and | Cyproconazole | 100:1 | 10:1 | 5:1 | 2:1 | 1:1 | 1:2 | 1:5 | 1:10 | 1:100 |
| C-19 | A | and | Propiconazole | 100:1 | 10:1 | 5:1 | 2:1 | 1:1 | 1:2 | 1:5 | 1:10 | 1:100 |
| C-20 | A | and | Fenoxanil | 100:1 | 10:1 | 5:1 | 2:1 | 1:1 | 1:2 | 1:5 | 1:10 | 1:100 |
| C-21 | A | and | Ferimzone | 100:1 | 10:1 | 5:1 | 2:1 | 1:1 | 1:2 | 1:5 | 1:10 | 1:100 |
| C-22 | A | and | Fthalide | 100:1 | 10:1 | 5:1 | 2:1 | 1:1 | 1:2 | 1:5 | 1:10 | 1:100 |
| C-23 | A | and | Kasugamycin | 100:1 | 10:1 | 5:1 | 2:1 | 1:1 | 1:2 | 1:5 | 1:10 | 1:100 |
| C-24 | A | and | Picoxystrobin | 100:1 | 10:1 | 5:1 | 2:1 | 1:1 | 1:2 | 1:5 | 1:10 | 1:100 |
| C-25 | A | and | Penthiopyrad | 100:1 | 10:1 | 5:1 | 2:1 | 1:1 | 1:2 | 1:5 | 1:10 | 1:100 |
| C-26 | A | and | Famoxadone | 100:1 | 10:1 | 5:1 | 2:1 | 1:1 | 1:2 | 1:5 | 1:10 | 1:100 |
| C-27 | A | and | Cymoxanil | 100:1 | 10:1 | 5:1 | 2:1 | 1:1 | 1:2 | 1:5 | 1:10 | 1:100 |
| C-28 | A | and | Proquinazid | 100:1 | 10:1 | 5:1 | 2:1 | 1:1 | 1:2 | 1:5 | 1:10 | 1:100 |
| C-29 | A | and | Flusilazole | 100:1 | 10:1 | 5:1 | 2:1 | 1:1 | 1:2 | 1:5 | 1:10 | 1:100 |
| C-30 | A | and | Mancozeb | 100:1 | 10:1 | 5:1 | 2:1 | 1:1 | 1:2 | 1:5 | 1:10 | 1:100 |
| C-31 | A | and | Copper hydroxide | 100:1 | 10:1 | 5:1 | 2:1 | 1:1 | 1:2 | 1:5 | 1:10 | 1:100 |
| C-32 | A | and | Fluopyram | 100:1 | 10:1 | 5:1 | 2:1 | 1:1 | 1:2 | 1:5 | 1:10 | 1:100 |
| C-33 | A | and | (a) | 100:1 | 10:1 | 5:1 | 2:1 | 1:1 | 1:2 | 1:5 | 1:10 | 1:100 |

(a) 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone Invertebrate pests are controlled in agronomic and nonagronomic applications by applying a solid form of Compound 1, typically in the form of a composition, in a biologically effective amount, to the environment of the pests, including the agronomic and/or nonagronomic locus of infestation, to the area to be protected, or directly on the pests to be controlled.

Thus the present invention comprises a method for controlling a invertebrate pest in agronomic and/or nonagronomic applications, comprising contacting the invertebrate pest or its environment with a biologically effective amount of a solid form of Compound 1 or with a composition comprising at least one such compound or a composition comprising at least one such compound and at least one additional biologically active compound or agent. Examples of suitable compositions comprising a solid form of Compound 1 and at least one additional biologically active compound or agent include granular compositions wherein the additional active compound is present on the same granule as the compound of the invention or on granules separate from those of the compound of the invention.

Embodiments of the method of this invention include contacting the environment. Of note is the method wherein the environment is a plant. Also of note is the method wherein the environment is an animal. Also of note is the method wherein the environment is a seed.

To achieve contact with a solid form of Compound 1 or composition of the invention to protect a field crop from invertebrate pest, the solid form of Compound 1 or composition is typically applied to the seed of the crop before planting, to the foliage (e.g., leaves, stems, flowers, fruits) of crop plants, or to the soil or other growth medium before or after the crop is planted.

One embodiment of a method of contact is by spraying. Alternatively, a granular composition comprising a compound of the invention can be applied to the plant foliage or the soil. Solid forms of Compound 1 can also be effectively delivered through plant uptake by contacting the plant with a composition comprising a compound of this invention applied as a soil drench of a liquid formulation, a granular formulation to the soil, a nursery box treatment or a dip of transplants. Of note is a composition of the present invention in the form of a soil drench liquid formulation. Also of note is a method for controlling a invertebrate pest comprising contacting the invertebrate pest or its environment with a biologically effective amount of a solid form of Compound 1 or with a composition comprising a biologically effective amount of a solid form of Compound 1. Of further note is this method wherein the environment is soil and the composition is applied to the soil as a soil drench formulation. Of further note is that solid forms of Compound 1 are also effective by localized application to the locus of infestation. Other methods of contact include application of a solid form of Compound 1 or a composition of the invention by direct and residual sprays, aerial sprays, gels, seed coatings, microencapsulations, systemic uptake, baits, ear tags, boluses, foggers, fumigants, aerosols, dusts and many others. One embodiment of a method of contact involves a dimensionally stable fertilizer granule, stick or tablet comprising a solid form of Compound 1 or composition of the invention. The solid forms of Compound 1 can also be impregnated into materials for fabricating invertebrate control devices (e.g., insect netting).

Solid forms of Compound 1 are also useful in seed treatments for protecting seeds from invertebrate pest. In the context of the present disclosure and claims, treating a seed means contacting the seed with a biologically effective amount of a solid form of Compound 1 which is typically formulated as a composition of the invention. This seed treatment protects the seed from invertebrate soil pests and generally can also protect roots and other plant parts in contact with the soil of the seedling developing from the germinating seed. The seed treatment may also provide protection of foliage by translocation of Compound 1 or a second active ingredient within the developing plant. Seed treatments can be applied to all types of seeds, including those from which plants genetically transformed to express specialized traits will germinate. Representative examples of genetically transformed plants include those expressing proteins toxic to parasitic nematodes, such as *Bacillus thuringiensis* toxin or those expressing herbicide resistance such as glyphosate acetyltransferase, which provides resistance to glyphosate.

One method of seed treatment is by spraying or dusting the seed with a solid form of Compound 1 (i.e. as a formulated composition) before sowing the seeds. Compositions formulated for seed treatment generally comprise a film former or adhesive agent. Therefore typically a seed coating composition of the present invention comprises a biologically effective amount of a solid form of Compound 1 and a film former or adhesive agent. Seed can be coated by spraying a flowable suspension concentrate directly into a tumbling bed of seeds and then drying the seeds. Alternatively, other formulation types such as wetted powders, solutions, suspo-emulsions, emulsifiable concentrates and emulsions in water can be sprayed on the seed. This process is particularly useful for applying film coatings on seeds. Various coating machines and processes are available to one skilled in the art. Suitable processes include those listed in P. Kosters et al., *Seed Treatment: Progress and Prospects*, 1994 BCPC Monograph No. 57, and references listed therein.

Solid forms of Compound 1 and their compositions, both alone and in combination with other insecticides, nematicides, and fungicides, are particularly useful in seed treatment for crops including, but not limited to, maize or corn, soybeans, cotton, cereal (e.g., wheat, oats, barley, rye and rice), potatoes, vegetables and oilseed rape.

Other insecticides or nematicides with which Solid forms of Compound 1 can be formulated to provide mixtures useful in seed treatment include but are not limited to abamectin, acetamiprid, acrinathrin, amitraz, avermectin, azadirachtin, bensultap, bifenthrin, buprofezin, cadusafos, carbaryl, carbofuran, cartap, chlorantraniliprole, chlorfenapyr, chlorpyrifos, clothianidin, cyantraniliprole, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, flufenoxuron, fluvalinate, formetanate, fosthiazate, hexaflumuron, hydramethylnon, imidacloprid, indoxacarb, lufenuron, metaflumizone, methiocarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, sulfoxaflor, tebufenozide, tetramethrin, thiacloprid, thiamethoxam, thiodicarb, thiosultap-sodium, tralomethrin, triazamate, triflumuron, *Bacillus thuringiensis* delta-endotoxins, all strains of *Bacillus thuringiensis* and all strains of Nucleo polyhydrosis viruses.

Fungicides with which Solid forms of Compound 1 can be formulated to provide mixtures useful in seed treatment include but are not limited to amisulbrom, azoxystrobin, boscalid, carbendazim, carboxin, cymoxanil, cyproconazole, difenoconazole, dimethomorph, fluazinam, fludioxonil, fluquinconazole, fluopicolide, fluoxastrobin, flutriafol, fluxapyroxad, ipconazole, iprodione, metalaxyl, mefenoxam, metconazole, myclobutanil, paclobutrazole, penflufen, picoxystrobin, prothioconazole, pyraclostrobin, sedaxane, silthiofam, tebuconazole, thiabendazole, thiophanate-methyl, thiram, trifloxystrobin and triticonazole.

Compositions comprising Solid forms of Compound 1 useful for seed treatment can further comprise bacteria and fungi that have the ability to provide protection from the harmful effects of plant pathogenic fungi or bacteria and/or soil born animals such as nematodes. Bacteria exhibiting nematicidal properties may include but are not limited to *Bacillus firmus, Bacillus cereus, Bacillius subtiliis* and *Pasteuria penetrans*. A suitable *Bacillus firmus* strain is strain CNCM I-1582 (GB-126) which is commercially available as BioNem™. A suitable *Bacillus cereus* strain is strain NCMM I-1592. Both *Bacillus* strains are disclosed in U.S. Pat. No. 6,406,690. Other suitable bacteria exhibiting nematicidal activity are *B. amyloliquefaciens* IN937a and *B. subtilis* strain GB03. Bacteria exhibiting fungicidal properties may include but are not limited to *B. pumilus* strain GB34. Fungal species exhibiting nematicidal properties may include but are not limited to *Myrothecium verrucaria, Paecilomyces lilacinus* and *Purpureocillium lilacinum*.

Seed treatments can also include one or more nematicidal agents of natural origin such as the elicitor protein called harpin which is isolated from certain bacterial plant pathogens such as *Erwinia amylovora*. An example is the Harpin-N-Tek seed treatment technology available as N-Hibit™ Gold CST.

Seed treatments can also include one or more species of legume-root nodulating bacteria such as the microsymbiotic nitrogen-fixing bacteria *Bradyrhizobium japonicum*. These inocculants can optionally include one or more lipo-chitooligosaccharides (LCDs), which are nodulation (Nod) factors produced by rhizobia bacteria during the initiation of nodule formation on the roots of legumes. For example, the Optimize® brand seed treatment technology incorporates LCO Promoter Technology™ in combination with an inocculant.

Seed treatments can also include one or more isoflavones which can increase the level of root colonization by mycorrhizal fungi. Mycorrhizal fungi improve plant growth by enhancing the root uptake of nutrients such as water, sulfates, nitrates, phosphates and metals. Examples of isoflavones include, but are not limited to, genistein, biochanin A, formononetin, daidzein, glycitein, hesperetin, naringenin and pratensein. Formononetin is available as an active ingredient in mycorrhizal inocculant products such as PHC Colonize® AG.

Seed treatments can also include one or more plant activators that induce systemic acquired resistance in plants following contact by a pathogen. An example of a plant activator which induces such protective mechanisms is acibenzolar-S-methyl.

The treated seed typically comprises a solid form of Compound 1 in an amount from about 0.1 g to 1 kg per 100 kg of seed (i.e. from about 0.0001 to 1% by weight of the seed before treatment). A flowable suspension formulated for seed treatment typically comprises from about 0.5 to about 70% of the active ingredient, from about 0.5 to about 30% of a film-forming adhesive, from about 0.5 to about 20% of a dispersing agent, from 0 to about 5% of a thickener, from 0 to about 5% of a pigment and/or dye, from 0 to about 2% of an antifoaming agent, from 0 to about 1% of a preservative, and from 0 to about 75% of a volatile liquid diluent.

Solid forms of Compound 1 can be incorporated into a bait composition that is consumed by an invertebrate pest or used within a device such as a trap, bait station, and the like. Such a bait composition can be in the form of granules which comprise (a) active ingredients, namely a biologically effective amount of a solid form of Compound 1 (b) one or more food materials; optionally (c) an attractant, and optionally (d) one or more humectants. Of note are granules or bait compositions which comprise between about 0.001-5% active ingredients, about 40-99% food material and/or attractant; and optionally about 0.05-10% humectants, which are effective in controlling soil invertebrate pests at very low application rates, particularly at doses of active ingredient that are lethal by ingestion rather than by direct contact. Some food materials can function both as a food source and an attractant. Food materials include carbohydrates, proteins and lipids. Examples of food materials are vegetable flour, sugar, starches, animal fat, vegetable oil, yeast extracts and milk solids. Examples of attractants are odorants and flavorants, such as fruit or plant extracts, perfume, or other animal or plant component, pheromones or other agents known to attract a target invertebrate pest. Examples of humectants, i.e. moisture retaining agents, are glycols and other polyols, glycerine and sorbitol. Of note is a bait composition (and a method utilizing such a bait composition) used to control at least one invertebrate pest selected from the group consisting of ants, termites and cockroaches. A device for controlling an invertebrate pest can comprise the present bait composition and a housing adapted to receive the bait composition, wherein the housing has at least one opening sized to permit the invertebrate pest to pass through the opening so the invertebrate pest can gain access to the bait composition from a location outside the housing, and wherein the housing is further adapted to be placed in or near a locus of potential or known activity for the invertebrate pest.

Solid forms of Compound 1 can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of a compound of the present invention. Combinations with spray oils, spray oil concentrations, spreader stickers, adjuvants, other solvents, and synergists such as piperonyl butoxide often enhance compound efficacy. For nonagronomic uses such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as needed for application. Of note is a spray composition comprising a biologically effective amount of a compound or a composition of the present invention and a carrier. One embodiment of such a spray composition comprises a biologically effective amount of a compound or a composition of the present invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one invertebrate pest selected from the group consisting of mosquitoes, black flies, stable flies, deer flies, horse flies, wasps, yellow jackets, hornets, ticks, spiders, ants, gnats, and the like, including individually or in combinations.

Nonagronomic uses refer to invertebrate pest control in the areas other than fields of crop plants. Nonagronomic uses of the present compounds and compositions include control of invertebrate pests in stored grains, beans and other foodstuffs, and in textiles such as clothing and carpets. Nonagronomic uses of the present compounds and compositions also include invertebrate pest control in ornamental plants, forests, in yards, along roadsides and railroad rights of way, and on turf such as lawns, golf courses and pastures. Nonagronomic uses of the present compounds and compositions also include invertebrate pest control in houses and other buildings which may be occupied by humans and/or companion, farm, ranch, zoo or other animals. Nonagronomic uses of the present compounds and compositions also include the control of pests such as termites that can damage wood or other structural materials used in buildings.

The solid forms of Compound 1 are also suitable for treatment of plant propagation material other than seed, such as fruit, tubers or plant seedlings. The propagation material can be treated with the compounds before planting, or the compounds can be applied to the planting site when the propagation material is being planted.

For agronomic applications, the rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredients per hectare are sufficient to control pests in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of invertebrate pest control.

What is claimed is:

1. A polymorph of 1-[(2-chloro-5-thiazolyl)methyl]-3-(3,5-dichlorophenyl)-2-hydroxy-9-methyl-4-oxo-4H-pyrido[1,2-a]pyrimidinium inner salt designated Form A characterized by a room-temperature powder Cu(Kα1)-X-ray diffraction pattern having at least the 2θ reflection positions

| 2θ |
|---|
| 8.036 |
| 9.592 |
| 13.719 |
| 14.453 |
| 17.07 |
| 23.092 |
| 24.027 |
| 24.481 |
| 29.743 |
| 31.831. |

2. A polymorph of 1-[(2-chloro-5-thiazolyl)methyl]-3-(3,5-dichlorophenyl)-2-hydroxy-9-methyl-4-oxo-4H-pyrido[1,2-a]pyrimidinium inner salt designated Form B characterized by a room-temperature powder Cu(Kα1)-X-ray diffraction pattern having at least the 2θ reflection positions

| 2θ |
|---|
| 6.654 |
| 9.41 |
| 10.983 |
| 11.986 |
| 15.513 |
| 21.225 |
| 22.012 |
| 25.638 |
| 28.545 |
| 40.244. |

3. A composition for controlling invertebrate pests comprising (a) the polymorph Form A of claim 1 and (b) at least one additional component selected from the group consisting of surfactants, solid diluents and liquid carriers.

4. A composition for controlling invertebrate pests comprising (a) the polymorph Form A of claim 1 and (b) at least one other nematocide, insecticide or fungicide.

5. A method for preparing the polymorph Form A of claim 1 comprising forming a slurry with a solvent of one or more solid forms of 1-[(2-chloro-5-thiazolyl)methyl]-3-(3,5-dichlorophenyl)-2-hydroxy-9-methyl-4-oxo-4H-pyrido[1,2-a]pyrimidinium inner salt selected from the group of Form B, amorphous forms and mixtures of any of the foregoing with Form A, and maintaining the slurry while the solid forms of 1-[(2-chloro-5-thiazolyl)methyl]-3-(3,5-dichlorophenyl)-2-hydroxy-9-methyl-4-oxo-4H-pyrido[1,2-a]pyrimidinium inner salt convert to polymorph Form A.

6. The method of claim 5 wherein the solid forms of 1-[(2-chloro-5-thiazolyl)methyl]-3-(3,5-dichlorophenyl)-2-hydroxy-9-methyl-4-oxo-4H-pyrido[1,2-a]pyrimidinium inner salt comprises polymorph Form B.

7. The method of claim 5 wherein seed crystals of polymorph Form A of claim 1 are added to the slurry.

8. The method of claim 5 wherein the slurry is agitated.

9. The method of claim 5 wherein the slurry is agitated and heated to a temperature between 30° C. and the boiling point of the solvent.

10. The method of claim 5 wherein the solvent comprises one or more of water, a $C_4$-$C_8$ ester, a $C_2$-$C_4$ alkanol, a $C_3$-$C_8$ ketone, a $C_4$-$C_8$ ether, a $C_2$-$C_7$ nitrile or a $C_7$-$C_9$ aromatic hydrocarbon.

11. The method of claim 10 wherein the solvent comprises one or more of water, ethyl acetate, acetone, acetonitrile or toluene.

12. A method for preparing the polymorph Form A of claim 1 comprising,
(A) contacting 2-(3,5-dichlorophenyl)propanedioyl dichloride and N-[(2-chloro-5-thiazolyl)methyl]-3-methyl-2-pyridinamine in the presence of a first solvent to form a reaction mixture containing an intermediate solid form of 1-[(2-chloro-5-thiazolyl)methyl]-3-(3,5-dichlorophenyl)-2-hydroxy-9-methyl-4-oxo-4H-pyrido[1,2-a]pyrimidinium inner salt,
(B) optionally separating the intermediate solid form of 1-[(2-chloro-5-thiazolyl)methyl]-3-(3,5-dichlorophenyl)-2-hydroxy-9-methyl-4-oxo-4H-pyrido[1,2-a]pyrimidinium inner salt, and
(C) contacting the intermediate solid form of 1-[(2-chloro-5-thiazolyl)methyl]-3-(3,5-dichlorophenyl)-2-hydroxy-9-methyl-4-oxo-4H-pyrido[1,2-a]pyrimidinium inner salt with a second solvent, optionally heated to a temperature between 30° C. and the boiling point of the second solvent, to convert the intermediate solid form to the polymorph Form A of claim 1.

13. The method of claim 12 wherein the intermediate solid form of 1-[(2-chloro-5-thiazolyl)methyl]-3-(3,5-dichlorophenyl)-2-hydroxy-9-methyl-4-oxo-4H-pyrido[1,2-a]pyrimidinium inner salt is Form B of claim 2.

14. The method of claim 12 wherein in step (C) the intermediate solid form of 1-[(2-chloro-5-thiazolyl)methyl]-3-(3,5-dichlorophenyl)-2-hydroxy-9-methyl-4-oxo-4H-pyrido[1,2-a]pyrimidinium inner salt is contacted with seed crystals of polymorph Form A of claim 1.

15. The method of claim 12 wherein the first and second solvent comprises toluene and the second solvent is heated to a temperature between 90° C. and 110° C.

16. A method for preparing the polymorph Form A of claim 1 comprising, contacting 2-(3,5-dichlorophenyl)propanedioyl dichloride and N-[(2-chloro-5-thiazolyl)methyl]-3-methyl-2-pyridinamine in the presence of a solvent optionally heated to a temperature between 30° C. and the boiling point of the solvent to form a reaction mixture containing polymorph Form A of 1-[(2-chloro-5-thiazolyl)methyl]-3-(3,5-dichlorophenyl)-2-hydroxy-9-methyl-4-oxo-4H -pyrido[1,2-a]pyrimidinium inner salt.

17. The method of claim 16 wherein the solvent comprises dichloromethane.

18. A method for controlling invertebrate pests comprising applying to the plant or seed, or to the environment of the plant or seed, a biologically effective amount of 1-[(2-chloro-5-thiazolyl)methyl]-3-(3,5-dichlorophenyl)-2-hydroxy-9-methyl-4-oxo-4H-pyrido[1,2-a]pyrimidinium inner salt comprising the polymorph Form A of claim 1.

* * * * *